United States Patent
Wang et al.

(10) Patent No.: US 10,800,742 B2
(45) Date of Patent: Oct. 13, 2020

(54) SMALL MOLECULE COMPOUNDS TARGETING PBX1 TRANSCRIPTIONAL COMPLEX

(71) Applicant: THE JOHNS HOPKINS UNIVERSITY, Baltimore, MD (US)

(72) Inventors: Tian-Li Wang, Clarksville, MD (US); Ie-Ming Shih, Clarksville, MD (US); Mark Vaal, Perry Hall, MD (US); Alexander Stoeck, Washington, DC (US); Jin G. Jung, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/568,956

(22) PCT Filed: Apr. 22, 2016

(86) PCT No.: PCT/US2016/028782
§ 371 (c)(1),
(2) Date: Oct. 24, 2017

(87) PCT Pub. No.: WO2016/172437
PCT Pub. Date: Oct. 27, 2016

(65) Prior Publication Data
US 2018/0118688 A1    May 3, 2018

Related U.S. Application Data

(60) Provisional application No. 62/152,314, filed on Apr. 24, 2015.

(51) Int. Cl.
| | |
|---|---|
| *C07C 237/40* | (2006.01) |
| *C07D 215/38* | (2006.01) |
| *A61K 31/167* | (2006.01) |
| *A61K 31/47* | (2006.01) |
| *A61P 35/00* | (2006.01) |
| *C07D 215/16* | (2006.01) |
| *C07D 215/20* | (2006.01) |
| *C07D 311/64* | (2006.01) |
| *A61P 25/28* | (2006.01) |
| *A61P 29/00* | (2006.01) |
| *C07C 311/21* | (2006.01) |

(52) U.S. Cl.
CPC .......... *C07D 215/38* (2013.01); *A61K 31/167* (2013.01); *A61K 31/47* (2013.01); *A61P 25/28* (2018.01); *A61P 29/00* (2018.01); *A61P 35/00* (2018.01); *C07C 237/40* (2013.01); *C07C 311/21* (2013.01); *C07D 215/16* (2013.01); *C07D 215/20* (2013.01); *C07D 311/64* (2013.01)

(58) Field of Classification Search
CPC .. C07D 215/38; C07D 215/16; C07D 215/20; C07D 311/64; A61K 31/167; A61K 31/47; C07C 237/40; C07C 311/21
See application file for complete search history.

(56) References Cited

U.S. PATENT DOCUMENTS

| | | | |
|---|---|---|---|
| 4,845,022 A | 7/1989 | Wolff | |
| 7,662,750 B2 | 2/2010 | Hangauer et al. | |
| 7,728,105 B2 | 6/2010 | Morgan et al. | |
| 2005/0153366 A1* | 7/2005 | Hangauer | ............ C07C 235/66 |
| | | | 506/15 |
| 2006/0234938 A1 | 10/2006 | Morgan et al. | |
| 2009/0163545 A1 | 6/2009 | Goldfarb | |

FOREIGN PATENT DOCUMENTS

| | | |
|---|---|---|
| WO | 2003019183 A1 | 3/2003 |
| WO | 2004-009533 A1 | 1/2004 |
| WO | 2004009533 A1 | 1/2004 |
| WO | 2004055049 A1 | 7/2004 |
| WO | 2005-049820 A1 | 6/2005 |
| WO | 2005049820 A1 | 6/2005 |
| WO | 2005057171 A2 | 6/2005 |
| WO | 2012-059442 A2 | 5/2012 |
| WO | 2012059442 A2 | 5/2012 |
| WO | 2013113489 A1 | 8/2013 |

OTHER PUBLICATIONS

Ji et al. Bioorg. Med. Chem. Lett. 2004, 14, 3875-3879.*
Morgan, et al., Antagonism of HOX/PBX dimer formation blocks the in vivo proliferation of melanoma. Cancer Res. Jun. 15, 2007;67(12):5806-13.
Charboneau, et al., Pbx1 is required for Hox D3-mediated angiogenesis. Angiogenesis. 2005;8(4):289-96.
Slupsky, et al., The HoxB1 hexapeptide is a prefolded domain: implications for the Pbx1/Hox interaction. Protein Sci Jun. 2001;10(6):1244-53.
Subramaniam, et al., Receptor interacting protein RIP140 inhibits both positive and negative gene regulation by glucocorticoids. J Biol Chem. Jun. 18, 1999;274(25)18121-7.
Cortez, et al., Advances in ovarian cancer therapy. Cancer Chemother Pharmacol. Jan. 2018;81(1):17-38.
Ho, et al., Developmental exposure to estradiol and bisphenol A increases susceptibility to prostate carcinogenesis and epigenetically regulates phosphodiesterase type 4 variant 4. Cancer Res. Jun. 1, 2006;66(11):5624-32.
Risolino, et al., Transcription factor PREP1 induces EMT and metastasis by controlling the TGF-β-SMAD3 pathway in non-small cell lung adenocarcinoma. Proc Natl Acad Sci U S A. Sep. 9, 2014;111(36):E3775-84.

(Continued)

*Primary Examiner* — Irina Neagu
(74) *Attorney, Agent, or Firm* — John Hopkins Technology Ventures

(57) ABSTRACT

In accordance with one or more embodiments, the present invention provides a compound of formulas I, II, and III, for use in methods of inhibition of PBX1-DNA interaction in a mammalian cell or population of cells, and for use in the treatment of medical conditions including but not limited to cancers, developmental disorders, inflammatory disorders, autoimmune diseases, or neuro-degenerative disorders.

10 Claims, 13 Drawing Sheets

(56) References Cited

OTHER PUBLICATIONS

Thiaville, et al., Identification of PBX1 Target Genes in Cancer Cells by Global Mapping of PBX1 Binding Sites. PLoS One. 2012; 7(5): e36054.
Chen, et al., Jagged1 expression regulated by Notch3 and Wnt/β-catenin signaling pathways in ovarian cancer. Oncotarget. Jul. 2010;1(3):210-8.
Park, et al., Notch3 overexpression is related to the recurrence of ovarian cancer and confers resistance to carboplatin. Am J Pathol. Sep. 2010;177(3):1087-94.
Chen, et al., Defining NOTCH3 target genes in ovarian cancer. Cancer Res. May 1, 2012;72(9):2294-303.
Ji, et al., Privileged scaffolds for blocking protein-protein interactions: 1,4-disubstituted naphthalene antagonists of transcription factor complex HOX-PBX/DNA. Bioorg Med Chem Lett. Aug. 2, 2004;14(15):3875-9.
Morgan, et al., Targeting HOX and PBX transcription factors in ovarian cancer. BMC Cancer. Mar. 10, 2010;10:89.
Magnani, et al., PBX1 genomic pioneer function drives ERα signaling underlying progression in breast cancer. PLoS Genet. Nov. 2011;7(11):e1002368.
Patani, et al., Bioisosterism: A Rational Approach in Drug Design. Chem Rev. Dec. 19, 1996;96(8):3147-3176.
Knoepfler, et al., The pentapeptide motif of Hox proteins is required for cooperative DNA binding with Pbx1, physically contacts Pbx1, and enhances DNA binding by Pbx1. Mol Cell Biol. Oct. 1995; 15(10): 5811-5819.
Dixon, et al., Preparation of a series of substituted fluoromethylnaphthalenes. Canadian J Chem. Jan. 1981;59:2629-41.
Knoepfler, et al., The pentapeptide motif of Hox proteins is required for cooperative DNA binding with Pbx1, physically contacts Pbx1, and enhances DNA binding by Pbx1. Mol Cell Biol. Oct. 1995;15(10):5811-9.
Evans, et al., Methods for drug discovery: development of potent, selective, orally effective cholecystokinin antagonists. J Med Chem. Dec. 1988;31(12):2235-46.
Patchett, et al., Chapter 26. Privileged structures—An update. Annual Reports in Med Chem. 2000;35:289-298.
Horton, et al., The combinatorial synthesis of bicyclic privileged structures or privileged substructures. Chem Rev. Mar. 2003;103(3):893-930.
Nicolaou, et al., Natural Product-like Combinatorial Libraries Based on Privileged Structures. 1. General Principles and Solid-Phase Synthesis of Benzopyrans. J Am Chem Soc. 2000;122(41):9939-9953.
Murzin, et al., How far divergent evolution goes in proteins. Curr Opin Struct Biol. Jun. 1998;8(3):380-387.
Gadek, et al., Small molecule antagonists of proteins. Biochem Pharmacol. Jan. 1, 2003;65(1):1-8.
Toogood, et al., Inhibition of protein-protein association by small molecules: approaches and progress. J Med Chem. Apr. 11, 2002;45(8):1543-58.
Cochran, et al., Antagonists of protein-protein interactions. Chem Biol. Apr. 2000;7(4):R85-94.
Boger, et al., Solution-phase combinatorial libraries: modulating cellular signaling by targeting protein-protein or protein-DNA interactions. Angew Chem Int Ed Engl. Sep. 15, 2003;42(35):4138-76.
Bogan, et al., Anatomy of hot spots in protein interfaces. J Mol Biol. Jul. 3, 1998;280(1):1-9.
Wolgerger, et al., Multiprotein-DNA complexes in transcriptional regulation. Annu Rev Biophys Biomol Struct. 1999;28:29-56.
Emery, et al., Therapeutic modulation of transcription factor activity. Trends Pharmacol Sci. May 2001;22(5):233-40.
Karamouzis, et al., Transcription Factors and Neoplasia: Vistas in Novel Drug Design. Clin Cancer Res. May 2002;8(5):949-61.
Scott, Vertebrate homeobox gene nomenclature. Cell. Nov. 13, 1992;71(4):551-3.
Knoepfler, et al., The Pbx family of proteins is strongly upregulated by a post-transcriptional mechanism during retinoic acid-induced differentiation of P19 embryonal carcinoma cells. Mech Dev. Apr. 1997;63(1):5-14.
Van Oostveen, et al. The role of homeobox genes in normal hematopoiesis and hematological malignancies. Leukemia. Nov. 1999;13(11):1675-90.
Maroulakou, et al., The study of HOX gene function in hematopoietic, breast and lung carcinogenesis. Anticancer Res. May-Jun. 2003;23(3A):2101-10.
Berg, Modulation of protein-protein interactions with small organic molecules. Angew Chem Int Ed Engl. Jun. 6, 2003;42(22)1462-81.
Piper, et al., Structure of a HoxB1-Pbx1 heterodimer bound to DNA: role of the hexapeptide and a fourth homeodomain helix in complex formation. Cell. Feb. 19, 1999;96(4):587-97.
Lipinski, et al., Experimental and computational approaches to estimate solubility and permeability in drug discovery and development settings. Adv Drug Delivery Rev. Jan. 1997;23(1-3):3-25.
Veber, et al., Molecular properties that influence the oral bioavailability of drug candidates. J Med Chem. Jun. 6, 2002;45(12):2615-23.
Ahmed, et al., Synthesis of a potent (±)-4-(2-hydroxyphenyl) analogue of the acromelic acids by dearomatising cyclisation of a lithiated N-p-methoxybenzyl-4-methoxy-1-naphthamide. Tetrahedron Letters. May 2001;42(20):3407-3410.
Node, et al., Hard acid and soft nucleophile system. 2. Demethylation of methyl ethers of alcohol and phenol with an aluminum halide-thiol system. J Org Chem. 1980;45(22):4275-4277.
McEvilly, et al., Transcriptional regulation of cortical neuron migration by POU domain factors. Science. Feb. 22, 2002;295(5559):1528-32.
Josephson, et al., POU transcription factors control expression of CNS stem cell-specific genes. Development. Aug. 1998;125(16):3087-100.
Hara, et al., Structure and evolution of four POU domain genes expressed in mouse brain. Proc Natl Acad Sci U S A. Apr. 15, 1992; 89(8): 3280-3284.
Pruitt, et al., Hox/Pbx and Brn binding sites mediate Pax3 expression in vitro and in vivo. Gene Expr Patterns. Oct. 2004;4(6):671-85.
Breinbauer, et al., From Protein Domains to Drug Candidates—Natural Products as Guiding Principles in the Design and Synthesis of Compound Libraries. Angew Chem Int Ed Engl. Aug. 16, 2002;41(16):2879-90.
Parlow, Syntheses of tetrahydronaphthalenes. Part II. Tetrahedron. Mar. 1994;50(11):3297-3314.
Fang, et al., Ytterbium Trichloride-Catalyzed Diels-Alder Reactions of Unactivated Dienes. Synthetic Communications. 2000; 30(15):2669-2676.
Birney, et al., Structural Investigations into the retro-Diels-Alder Reaction. Experimental and Theoretical Studies. J Am Chem Soc. 2002;124(18):5091-5099.
Boger, Solution-phase synthesis of combinatorial libraries designed to modulate protein-protein or protein-DNA Interactions. Bioorg Med Chem. Apr. 17, 2003;11(8):1607-13.
Bain, et al., From embryonal carcinoma cells to neurons: the P19 pathway. Bioessays. May 1994;16(5):343-8.
Shiraishi, et al., Pre-B-cell leukemia transcription factor 1 is a major target of promyelocytic leukemia zinc-finger-mediated melanoma cell growth suppression. Oncogene. Jan. 18, 2007;26(3):339-48.
Delval, et al., The Pbx interaction motif of Hoxa1 is essential for its oncogenic activity. PLoS One. 2011;6(9):e25247.
Nourse, et al., Chromosomal translocation t(1;19) results in synthesis of a homeobox fusion mRNA that codes for a potential chimeric transcription factor Cell. Feb. 23, 1990;60(4):535-45.
Kamps, et al., The human t(1;19) translocation in pre-B ALL produces multiple nuclear E2A-Pbx1 fusion proteins with differing transforming potentials. Genes Dev. Mar. 1991;5(3):358-68.

* cited by examiner

FIGURE 9
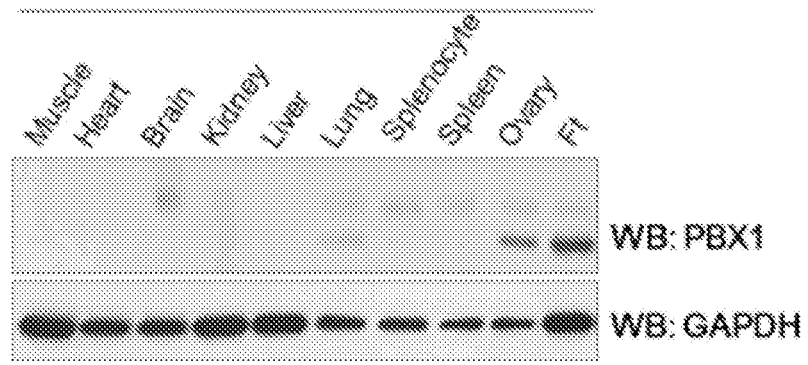
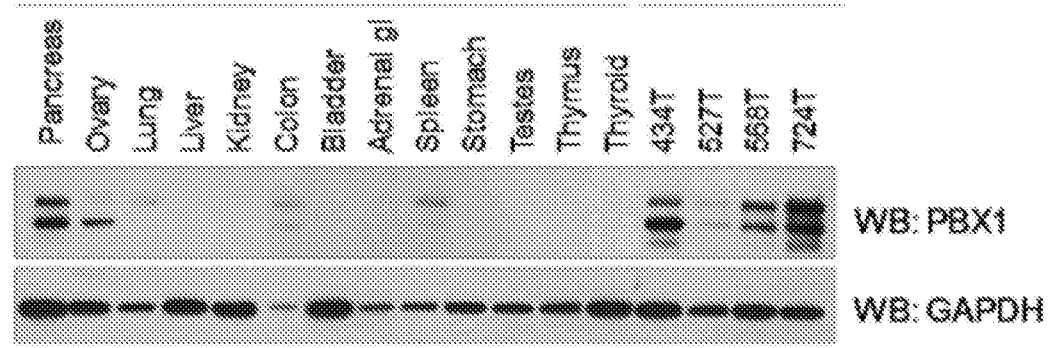

SMALL MOLECULE COMPOUNDS TARGETING PBX1 TRANSCRIPTIONAL COMPLEX

CROSS-REFERENCE TO RELATED APPLICATIONS

This application is a 35 U.S.C. § 371 U.S. national entry of International Application PCT/US2016/028782, having an international filing date of Apr. 22, 2016, which claims the benefit of U.S. Provisional Application No. 62/152,314, filed Apr. 24, 2015, the content of each of the aforementioned applications is herein incorporated by reference in their entirety.

STATEMENT OF GOVERNMENTAL INTEREST

This invention was made with government support under grant no. 1R01CA148826-01A1, awarded by the National Institutes of Health. The government has certain rights in the invention.

BACKGROUND OF THE INVENTION

PBX1 is a homeodomain protein that can interact with DNA and other homeodomain proteins such as Hox to form transcription complexes. In addition, recent ChIP-seq and ChIP-chip studies in human cancer cells have suggested that PBX1 can potentially bind to DNA as a monomer; a significant number of PBX1 direct target genes identified by the ChIP-seq and ChIP-chip studies demonstrated a single PBX1 binding motif rather than PBX1-HOX dual motifs 1, 2. The roles of PBX1 transcription in cancer were documented in breast cancer, ovarian cancer, prostate cancer (Prostate. 2006 Jul. 1;66(10): 1092-90), non-small cell lung adenocarcinoma (Proc Natl Acad Sci USA 2014 Sep. 9;111 (36):E 3775-84), and melanoma 3-5. Furthermore, frequent chromosomal translocation t(1;19), which leads to the creation of a chimeric protein, E2A-PBX1, was observed in pre-B-cell acute lymphoblastoid leukemia (ALL) 6, 7. Our goal is to develop small molecule compounds that can block PBX1-mediated transcription, which is critical to pathogenesis of a variety of cancers.

X-ray crystallographic studies have elucidated the PBX1 transcription complex in great detail, including revealing the interfaces between PBX1 and DNA and the interfaces between PBX1 and HOXB1 proteins 8. Strategies have previously been developed to target the interaction between the PBX1-HOX heterodimer proteins, with the understanding that it is mediated by the conserved Hox hexapeptide. These prior studies include employing a computer-guided structure design approach to dock 1,4-disubstituted naphthalenes to the binding pocket between the PBX-HOX protein-protein interaction interface 9. Another group has developed peptide-based antagonists mimicking the Hox hexapeptide that can potentially compete for interaction with PBX1 or other homeobox proteins 10, 11. However, the compounds or peptides developed from these approaches are currently restricted to in vitro usage due to their poor potency, suboptimal cellular penetration, and/or poor solubility. This unsatisfactory result is not surprising, as a protein-protein complex usually involves large interfaces between two proteins, and the interaction often involves multiple sites on each protein. Therefore, it is very difficult to use small molecules to effectively disrupt protein-protein complex. In fact, there are almost no small molecule compounds developed so far that can have the satisfactory potency for blocking the transcription protein complex. We posit that rather than blocking protein-protein interaction, directly interfering with PBX1-DNA interaction, which involves only a small number of amino acid residues on the PBX1 protein surface, is able to overcome the aforementioned problems and permits us to develop potent small molecule PBX1 inhibitors.

As such, there exists a need for small molecules which directly interfere with PBX1-DNA interaction, and thereby inhibit cancer growth.

SUMMARY OF THE INVENTION

In accordance with an embodiment, the present invention provides a compound of formula I:

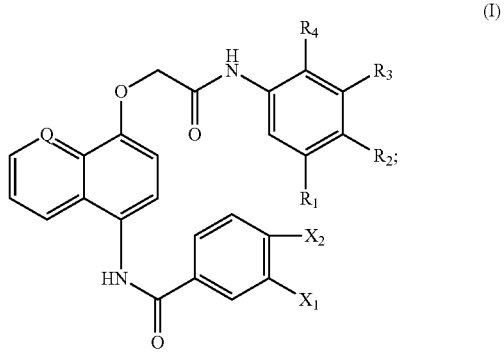

or a salt, solvate, or stereoisomer thereof, wherein $R_1$ to $R_4$ are independently H, OH or $OCH_3$, $X_1$ or $X_2$ is either H or a halogen, and Q is either CH or N.

In accordance with another embodiment, the present invention provides a compound of formula II having the following formula:

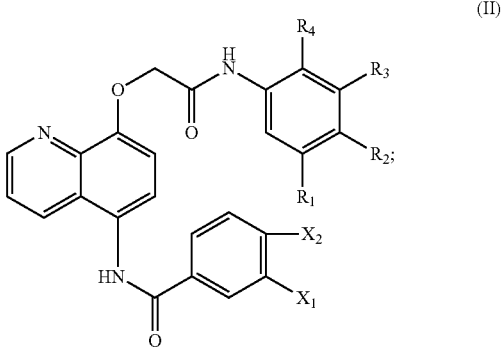

or a salt, solvate, or stereoisomer thereof, wherein $R_1$ to $R_4$ are independently H, OH or $OCH_3$, and $X_1$ or $X_2$ is either H or a halogen.

In accordance with another embodiment, the present invention provides a compound of Formula II, selected from the group consisting of:

(T362)

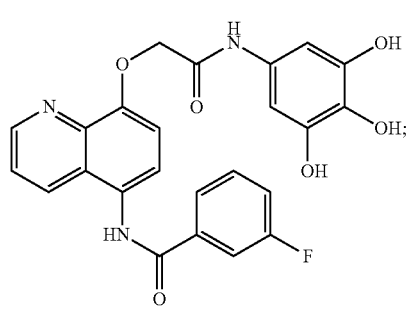

(T363)

(T364)

or a salt, solvate, or stereoisomer thereof.

In accordance with another embodiment, the present invention provides a compound of formula III having the following formula:

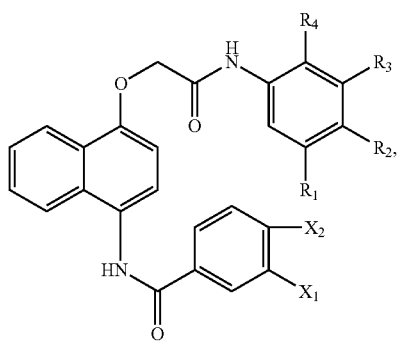

(III)

or a salt, solvate, or stereoisomer thereof, wherein $R_1$ to $R_4$ are independently H, OH or $OCH_3$, and $X_1$ or $X_2$ is either H or a halogen.

In accordance with another embodiment, the present invention provides a compound of Formula III, selected from the group consisting of:

(T383)

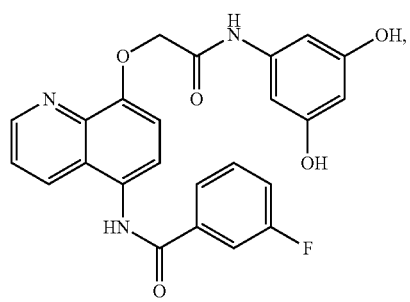

(T417)

(T418)

or a salt, solvate, or stereoisomer thereof.

In accordance with another embodiment, the present invention provides a compound having the following formula:

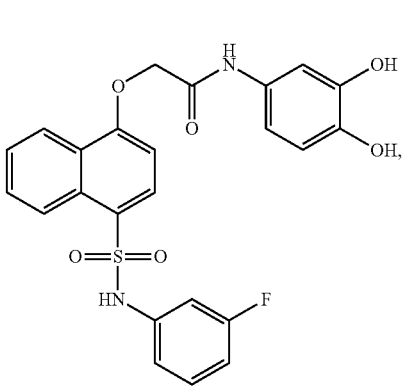

(T388)

or a salt, solvate, or stereoisomer thereof.

In accordance with an embodiment, the present invention provides a pharmaceutical composition comprising a compound of formula I:

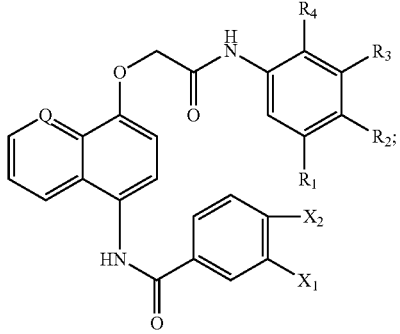
(I)

or a salt, solvate, or stereoisomer thereof, wherein $R_1$ to $R_4$ are independently H, OH or $OCH_3$, $X_1$ or $X_2$ is either H or a halogen, and Q is either CH or N, and a pharmaceutically acceptable carrier.

In accordance with a further embodiment, the present invention provides a pharmaceutical composition comprising a compound of formula II:

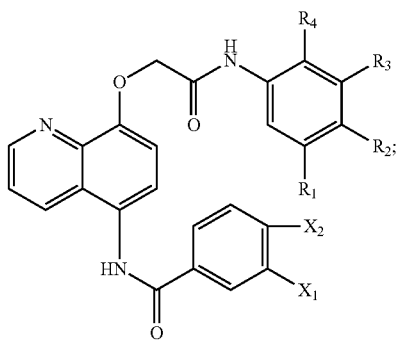
(II)

or a salt, solvate, or stereoisomer thereof, wherein $R_1$ to $R_4$ are independently H, OH or $OCH_3$, $X_1$ or $X_2$ is either H or a halogen, and a pharmaceutically acceptable carrier.

In accordance with another embodiment, the present invention provides a pharmaceutical composition comprising a compound of Formula II, selected from the group consisting of:

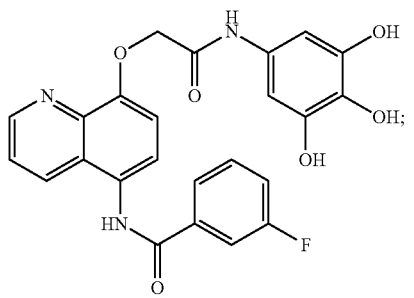
(T362)

-continued

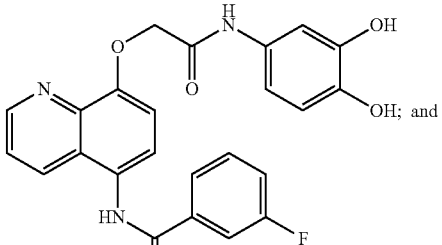
(T363)

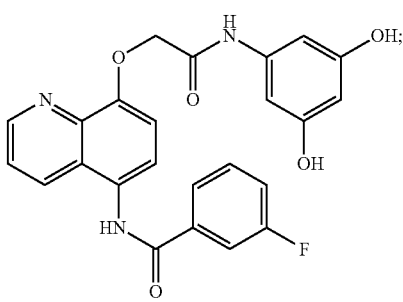
(T364)

or a salt, solvate, or stereoisomer thereof, and a pharmaceutically acceptable carrier.

In accordance with a further embodiment, the present invention provides a pharmaceutical composition comprising a compound of formula III:

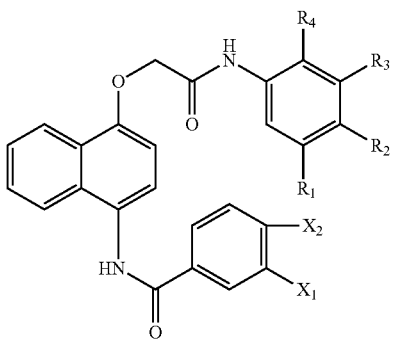
(III)

or a salt, solvate, or stereoisomer thereof, wherein $R_1$ to $R_4$ are independently H, OH or $OCH_3$, $X_1$ or $X_2$ is either H or a halogen, and a pharmaceutically acceptable carrier.

In accordance with another embodiment, the present invention provides a pharmaceutical composition comprising a compound of Formula III, selected from the group consisting of:

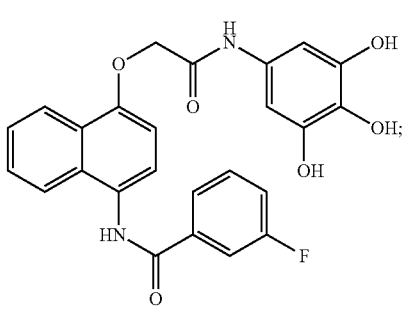
(T383)

(T417)

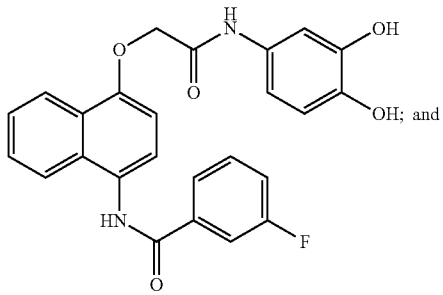

(T418)

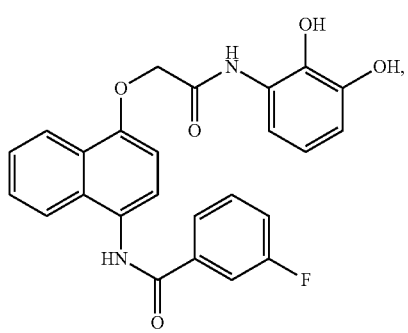

or a salt, solvate, or stereoisomer thereof, and a pharmaceutically acceptable carrier.

In accordance with another embodiment, the present invention provides a pharmaceutical composition comprising a compound having the following formula:

(T388)

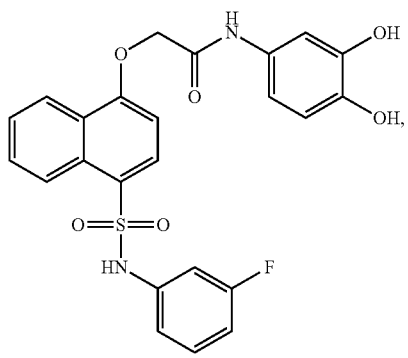

or a salt, solvate, or stereoisomer thereof, and a pharmaceutically acceptable carrier.

In accordance with an embodiment, the present invention provides a pharmaceutical composition comprising any of the compounds described above, at least one other biologically active agent, and a pharmaceutically acceptable carrier.

In accordance with an embodiment, the present invention provides a method of inhibition of PBX1-DNA interaction in a mammalian cell or population of cells, comprising contacting the cell or population of cells with any of the compounds described above or a pharmaceutical composition comprising any of the compounds described above.

In accordance with yet a further embodiment, the present invention provides a method for treating medical conditions including but not limited to cancers, developmental disorders, inflammatory disorders, autoimmune diseases, or neuro-degenerative disorders in a subject comprising administering to the subject a pharmaceutical composition comprising any of the compounds described above.

In accordance with an embodiment, the present invention provides a method for treating medical conditions including but not limited to cancers, developmental disorders, inflammatory disorders, autoimmune diseases, or neuro-degenerative disorders in a subject comprising administering to the subject a pharmaceutical composition comprising any of the compounds described above, and at least one other biologically active agent.

BRIEF DESCRIPTION OF THE DRAWINGS

FIG. 9 shows PBX1 protein expression in normal human and mouse tissues. Western blot was performed to determine the expression of PBX1 protein in a panel of human and mouse tissues. Human ovarian high-grade serious carcinoma (HGSC) tissues, which overexpress PBX1, were included as a comparison.

DETAILED DESCRIPTION OF THE INVENTION

Figure 1:
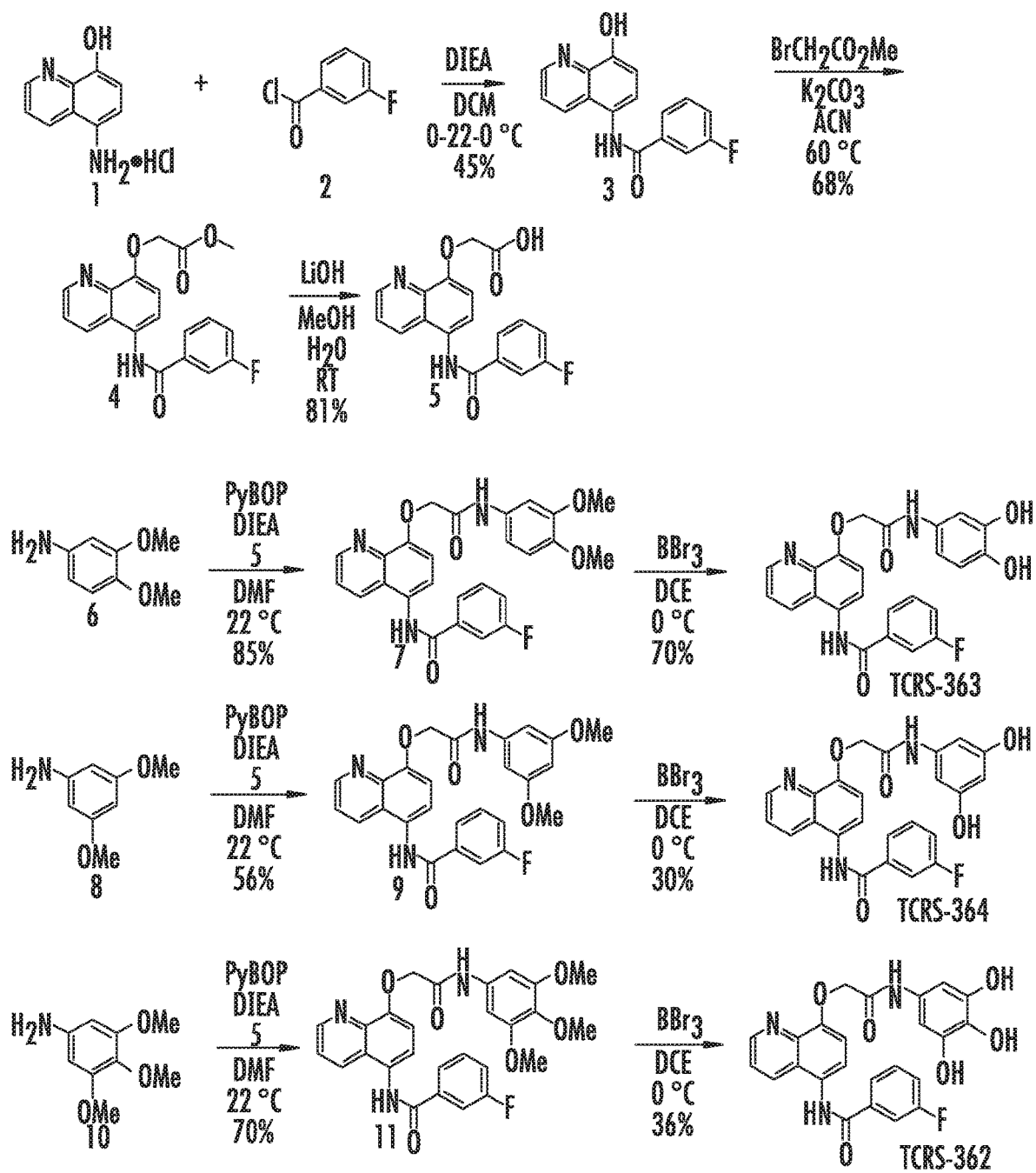
FIG. 1 is a schematic depicting the general synthesis of TCRS-362, TCRS-363, and TCRS-364.

Given the important function of PBX in human cancers, developmental disorders, inflammatory disorders, autoimmune diseases, and neuro-degenerative disorders, small molecular compounds that are capable of blocking the binding between PBX and DNA and/or destabilizing the PBX transcription complex as described herein can down-regulate the transcriptional signaling of PBX1 and potentially be useful for therapeutic interventions. In addition, PBX is involved in sustaining the pluripotency of stem cells; therefore, the small compounds developed herein can be applied for stem cell-related research and therapy.

The compounds and methods disclosed herein are the first to bring this novel class of molecular compounds to usefulness in preclinical and clinical studies because the inventive compounds reach satisfactory aqueous solubility in culture medium and have a low $IC_{50}$ in cytotoxicity assays. The compounds and methods of the present invention are the first to demonstrate efficacy in blocking PBX1-DNA interaction, suppressing PBX transcription, exhibiting cytotoxic effects in cancer cells with PBX1 overexpression and in vivo anti-tumor effects.

In accordance with an embodiment, the present invention provides a compound of formula I:

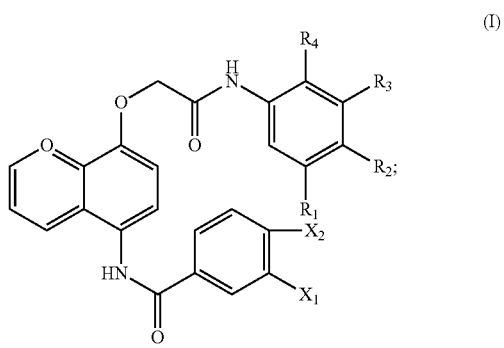

or a salt, solvate, or stereoisomer thereof, wherein $R_1$ to $R_4$ are independently H, OH or $OCH_3$, $X_1$ or $X_2$ is either H or a halogen, and Q is either CH or N.

In accordance with another embodiment, the present invention provides a compound of formula II having the following formula:

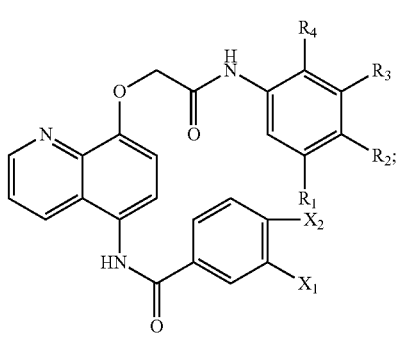

(II)

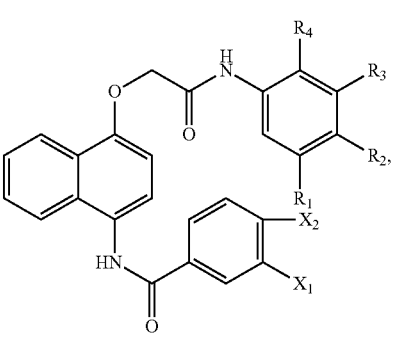

(III)

or a salt, solvate, or stereoisomer thereof, wherein $R_1$ to $R_4$ are independently H, OH or $OCH_3$, and $X_1$ or $X_2$ is either H or a halogen.

In accordance with another embodiment, the present invention provides a compound of Formula II, selected from the group consisting of:

or a salt, solvate, or stereoisomer thereof, wherein $R_1$ to $R_4$ are independently H, OH or $OCH_3$, and $X_1$ or $X_2$ is either H or a halogen.

In accordance with another embodiment, the present invention provides a compound of Formula III, selected from the group consisting of:

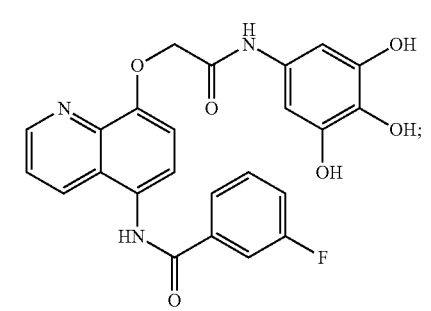

(T362)

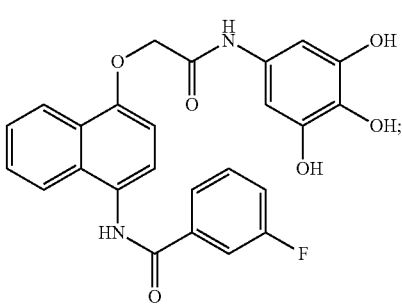

(T383)

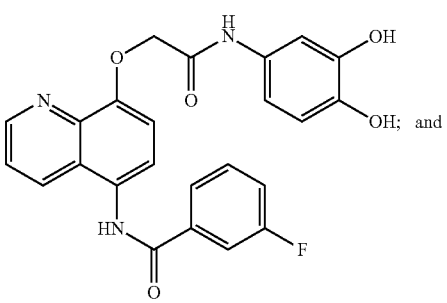

(T363)

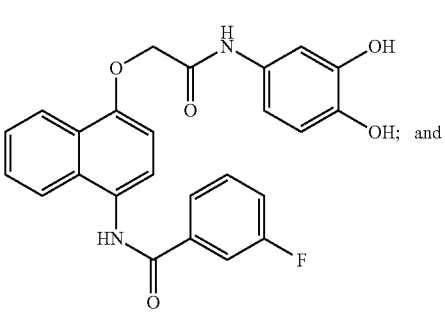

(T417)

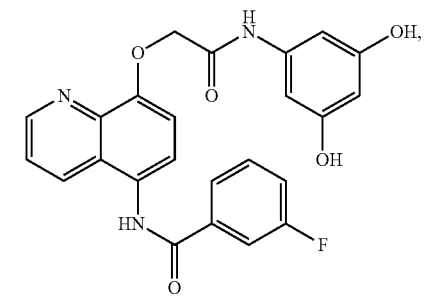

(T364)

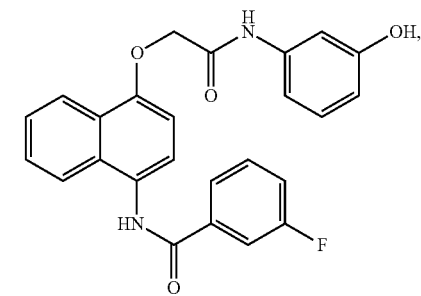

(T418)

or a salt, solvate, or stereoisomer thereof.

In accordance with another embodiment, the present invention provides a compound of formula III having the following formula:

or a salt, solvate, or stereoisomer thereof.

In accordance with another embodiment, the present invention provides a compound having the following formula:

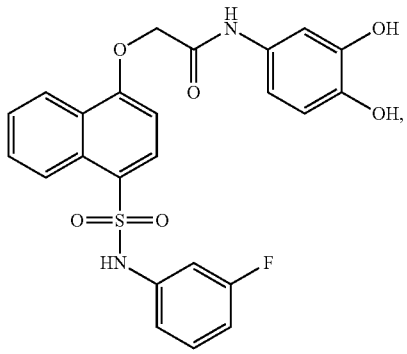
(T388)

or a salt, solvate, or stereoisomer thereof.

In accordance with an embodiment, the present invention provides a pharmaceutical composition comprising a compound of formula I:

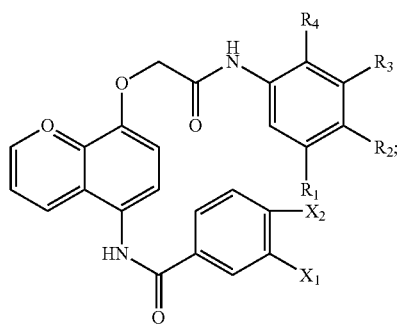
(I)

or a salt, solvate, or stereoisomer thereof, wherein $R_1$ to $R_4$ are independently H, OH or $OCH_3$, $X_1$ or $X_2$ is either H or a halogen, and Q is either CH or N, and a pharmaceutically acceptable carrier.

In accordance with a further embodiment, the present invention provides a pharmaceutical composition comprising a compound of formula II:

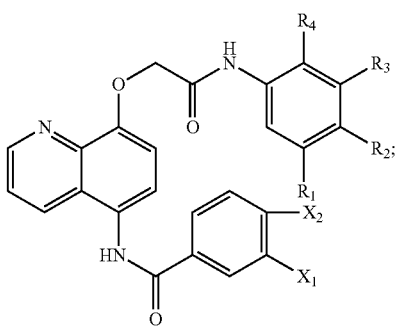
(II)

or a salt, solvate, or stereoisomer thereof, wherein $R_1$ to $R_4$ are independently H, OH or $OCH_3$, $X_1$ or $X_2$ is either H or a halogen, and a pharmaceutically acceptable carrier.

In accordance with another embodiment, the present invention provides a pharmaceutical composition comprising a compound of Formula II, selected from the group consisting of:

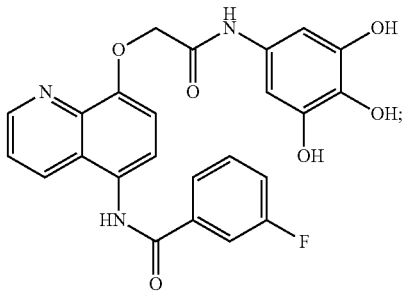
(T362)

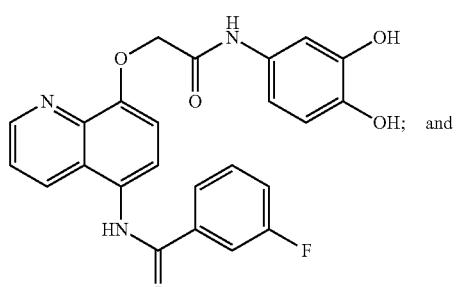
(T363)

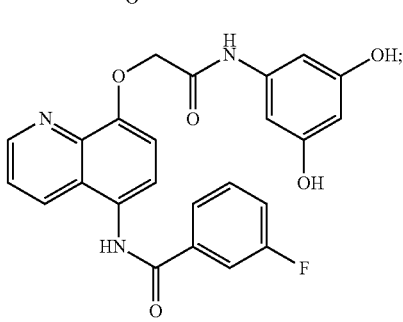
(T364)

or a salt, solvate, or stereoisomer thereof, and a pharmaceutically acceptable carrier.

In accordance with a further embodiment, the present invention provides a pharmaceutical composition comprising a compound of formula III:

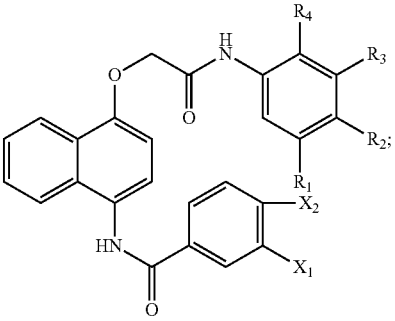
(III)

or a salt, solvate, or stereoisomer thereof, wherein $R_1$ to $R_4$ are independently H, OH or $OCH_3$, $X_1$ or $X_2$ is either H or a halogen, and a pharmaceutically acceptable carrier.

In accordance with another embodiment, the present invention provides a pharmaceutical composition comprising a compound of Formula III, selected from the group consisting of:

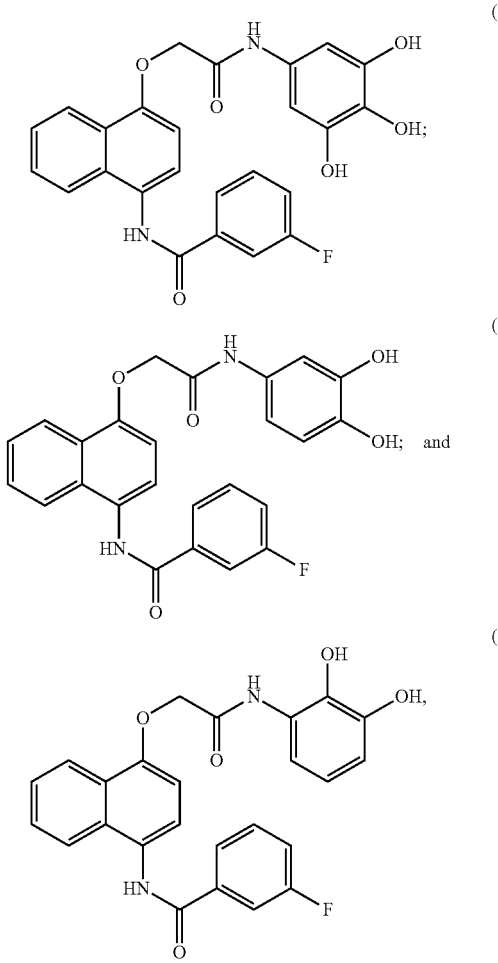

(T383)

(T417)

(T418)

or a salt, solvate, or stereoisomer thereof, and a pharmaceutically acceptable carrier.

In accordance with another embodiment, the present invention provides a pharmaceutical composition comprising a compound having the following formula:

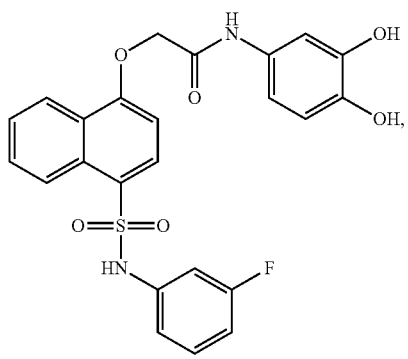

(T388)

or a salt, solvate, or stereoisomer thereof, and a pharmaceutically acceptable carrier.

In accordance with an embodiment, the present invention provides a pharmaceutical composition comprising a compound of formula I, at least one other biologically active agent, and a pharmaceutically acceptable carrier.

In accordance with an embodiment, the present invention provides a method of inhibition of PBX1-DNA interaction in a mammalian cell or population of cells, comprising contacting the cell or population of cells with a compound of formula I or a pharmaceutical composition comprising a compound of formula I.

In accordance with yet a further embodiment, the present invention provides a method for treating medical conditions including but not limited to cancers, developmental disorders, inflammatory disorders, autoimmune diseases, or neuro-degenerative disorders in a subject comprising administering to the subject a pharmaceutical composition comprising a compound of formula I.

In accordance with an embodiment, the present invention provides a method for treating medical conditions including but not limited to cancers, developmental disorders, inflammatory disorders, autoimmune diseases, or neuro-degenerative disorders in a subject comprising administering to the subject a pharmaceutical composition comprising a compound of formula I, and at least one other biologically active agent.

In accordance with an embodiment, the present invention provides a pharmaceutical composition comprising a compound of formula II, at least one other biologically active agent, and a pharmaceutically acceptable carrier.

In accordance with an embodiment, the present invention provides a method of inhibition of PBX1-DNA interaction in a mammalian cell or population of cells, comprising contacting the cell or population of cells with a compound of formula II or a pharmaceutical composition comprising a compound of formula II.

In accordance with yet a further embodiment, the present invention provides a method for treating medical conditions including but not limited to cancers, developmental disorders, inflammatory disorders, autoimmune diseases, or neuro-degenerative disorders in a subject comprising administering to the subject a pharmaceutical composition comprising a compound of formula II.

In accordance with an embodiment, the present invention provides a method for treating medical conditions including but not limited to cancers, developmental disorders, inflammatory disorders, autoimmune diseases, or neuro-degenerative disorders in a subject comprising administering to the subject a pharmaceutical composition comprising a compound of formula II, and at least one other biologically active agent.

In accordance with an embodiment, the present invention provides a pharmaceutical composition comprising a compound of formula III, at least one other biologically active agent, and a pharmaceutically acceptable carrier.

In accordance with an embodiment, the present invention provides a method of inhibition of PBX1-DNA interaction in a mammalian cell or population of cells, comprising contacting the cell or population of cells with a compound of formula III or a pharmaceutical composition comprising a compound of formula III.

In accordance with yet a further embodiment, the present invention provides a method for treating medical conditions including but not limited to cancers, developmental disorders, inflammatory disorders, autoimmune diseases, or neuro-degenerative disorders in a subject comprising administering to the subject a pharmaceutical composition comprising a compound of formula III.

In accordance with an embodiment, the present invention provides a method for treating cancer in a subject comprising administering to the subject a pharmaceutical composition comprising a compound of formula III, and at least one other biologically active agent.

In accordance with an embodiment, the present invention provides a pharmaceutical composition comprising compound T388, at least one other biologically active agent, and a pharmaceutically acceptable carrier.

In accordance with an embodiment, the present invention provides a method of inhibition of PBX1-DNA interaction in a mammalian cell or population of cells, comprising contacting the cell or population of cells with compound T388 or a pharmaceutical composition comprising compound T388.

In accordance with yet a further embodiment, the present invention provides a method for treating medical conditions including but not limited to cancers, developmental disorders, inflammatory disorders, autoimmune diseases, or neuro-degenerative disorders in a subject comprising administering to the subject a pharmaceutical composition comprising compound T388.

As used herein, the term "developmental disorders" can include autism spectrum disorder, motor or sensory impairments such as cerebral palsy and muscular dystrophy, for example.

As used herein, the term "inflammatory disease" can mean diseases such as atherosclerosis, ischemic heart disease, asthma, pelvic inflammatory disease, reperfusion injury, vasculitis, acne, glomerulonephritis and chronic prostatitis, for example.

As used herein, the term "autoimmune disease" can mean diseases including inflammatory bowel disease (e.g., ulcerative colitis or Crohn's disease), rheumatoid arthritis, diabetes mellitus, celiac disease, autoimmune thyroid disease, autoimmune liver disease, Addison's Disease, Sjögren's Syndrome, transplant rejection, graft vs. host disease and host vs. graft disease. In certain embodiments, the autoimmune disease is a neurological autoimmune disease, such as multiple sclerosis. In certain embodiments, the autoimmune disease is an inflammatory bowel disease, such as uncreative colitis or Crohn's disease. Examples of neurological autoimmune diseases include, for example, multiple sclerosis, Guillain-Barre syndrome, Lambert-Eaton myasthenic syndrome, myasthenia gravis, transverse myelitis, systemic lupus erythematosus (SLE or lupus), acute disseminated encephalomyelitis, vasculitis, Sjogren's syndrome, Graves' disease, autoimmune inner ear disease, narcolepsy, neuro-myotonia, and schizophrenia.

With respect to the inventive compositions and methods, the disease to be treated can include cancer. Cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

In accordance with an embodiment, the present invention provides a method for treating medical conditions including but not limited to cancers, developmental disorders, inflammatory disorders, autoimmune diseases, or neuro-degenerative disorders in a subject comprising administering to the subject a pharmaceutical composition comprising compound T388, and at least one other biologically active agent.

The biologically active agent may vary widely with the intended purpose for the composition. The term active is art-recognized and refers to any moiety that is a biologically, physiologically, or pharmacologically active substance that acts locally or systemically in a subject. Examples of biologically active agents, which may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released into a subject, for example, into adjacent tissues or fluids upon administration to a subject. In some embodiments, a biologically active agent may be used in a cross-linked polymer matrix of this invention, to, for example, promote cartilage formation. In other embodiments, a biologically active agent may be used in a cross-linked polymer matrix of this invention, to treat, ameliorate, inhibit, or prevent a disease or symptom, in conjunction with, for example, promoting cartilage formation.

Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compositions of the invention.

In certain embodiments, the subject compositions comprise about 1% to about 75% or more by weight of the total composition, alternatively about 2.5%, 5%, 10%, 20%, 30%, 40%, 50%, 60% or 70%, of a biologically active agent.

Non-limiting examples of biologically active agents include following: adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-co-agulants, anti-convulsants, anti-diarrheal, anti-emetics, anti-hypertensive agents, anti-infective agents, anti-inflammatory agents such as steroids, non-steroidal anti-inflammatory agents, anti-malarials, anti-manic agents, anti-nauseants, anti-neoplastic agents, anti-obesity agents, anti-parkinsonian agents, anti-pyretic and analgesic agents, anti-spasmodic agents, anti-thrombotic agents, anti-uricemic agents, anti-anginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, agents, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, pro-gestational agents, prostaglandins, psychic energizers, psychotropics, sedatives, stimulants, thyroid and anti-thyroid agents, tranquilizers, uterine relaxants, vitamins, antigenic materials, and prodrugs.

Specific examples of useful biologically active agents the above categories include: (a) anti-neoplastics such as androgen inhibitors, antimetabolites, cytotoxic agents, and immunomodulators; (b) anti-tussives such as dextromethorphan, hydrobromide, noscapine, carbetapentane citrate, and chlophedianol hydrochloride; (c) antihistamines such as chlorpheniramine phenindamine tartrate, pyrilamine doxylamine succinate, and phenyltoloxamine citrate; (d) decongestants such as hydrochloride, phenylpropanolamine hydrochloride, pseudoephedrine hydrochloride, and ephedrine; (e) various alkaloids such as codeine phosphate, codeine sulfate, and morphine; (f) mineral supplements such as potassium chloride, zinc chloride, calcium carbonate, magnesium oxide, and other alkali metal and alkaline earth metal salts; (g) ion exchange resins such as such as N-acetyl-procainamide; (h) antipyretics and analgesics such as acetaminophen, aspirin and ibuprofen; appetite suppressants such as phenyl-propanol amine or caffeine; (i) expectorants such as guaifenesin; (j) antacids such as aluminum hydroxide and magnesium hydroxide; biologicals such as peptides, polypeptides, proteins and amino acids, hormones, interferons or cytokines and other bioactive peptidic compounds, such as calcitonin, ANF, EPO and insulin; (k) anti-infective agents such as anti-fungals, anti-virals, antiseptics and antibiotics; and (l) desensitizing agents and antigenic materials, such as those useful for vaccine applications.

More specifically, non-limiting examples of useful biologically active agents include the following therapeutic categories: analgesics, such as nonsteroidal anti-inflammatory drugs, opiate agonists and salicylates; antihistamines, such as H1-blockers and H2-blockers; anti-infective agents, such as antihelmintics, antianaerobics, antibiotics, aminoglycoside antibiotics, antifungal antibiotics, cephalosporin antibiotics, macrolide antibiotics, miscellaneous antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, and urinary anti-infectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, a-blocker sympatholytics, sympatholytics, sympathomimetics, and adrenergic agonist sympathomimetics; cardiovascular agents, such as antianginals, antianginals, calcium-channel blocker antianginals, nitrate antianginals, antiarrhythmics, cardiac glycoside antiarrhythmics, class I antiarrhythmics, class antiarrhythmics, class antiarrhythmics, class IV antiarrhythmics, antihypertensive agents, a-blocker antihypertensives, angiotensin-converting enzyme inhibitor (ACE inhibitor) antihypertensives, 13-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, reductase inhibitor antilipemics, inotropes, cardiac glycoside inotropes, and thrombolytic agents; dermatological agents, such as antihistamines, anti-inflammatory agents, corticosteroid anti-inflammatory agents, anesthetics, topical anti-infectives, topical anti-infectives, antiviral topical anti-infectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, H2-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, anti-androgens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immunosuppressive anti-inflammatory agents, nonsteroidal anti-inflammatory drugs, salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, such as anti-glaucoma agents, anti-glaucoma agents, mitotics, anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs; psychotropic agents, such as antidepressants, heterocyclic antidepressants, monoamine oxidase inhibitors selective serotonin re-uptake inhibitors tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-intlammatory agents; toxicology agents, such as antidotes, heavy agents, substance abuse agents, deterrent substance abuse agents, and withdrawal substance abuse agents; minerals; and vitamins, such as vitamin A, vitamin B, vitamin C, vitamin D, vitamin E, and vitamin K.

Other classes of biologically active agents from the above categories include: (1) analgesics in general, such as lidocaine, other "caine" analgesics or derivatives thereof, and nonsteroidal anti-inflammatory drugs (NSAIDs) analgesics, including diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) H1-blocker antihistamines, such as clemastine and terfenadine; (5) H2-blocker antihistamines, such as cimetidine, famotidine, nizadine, and ranitidine; (6) anti-infective agents, such as mupirocin; (7) antianaerobic anti-infectives, such as chloramphenicol and clindamycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous antibiotic anti-infectives, such as and imipenem; penicillin, (11) antibiotic anti-infectives, such as nafcillin, oxacillin, penicillin G, and penicillin V; (12) quinolone antibiotic anti-infectives, such as ciprofloxacin and nortfloxacin; (13) tetracycline antibiotic anti-infectives, such as doxycycline, minocycline and tetracycline; (14) antituberculosis antimycobacterial anti-infectives such as isoniazid and rifampin; (15) anti-protozoal anti-infectives, such as atovaquone and dapsone; (16) antimalarial anti-protozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon-γ, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antineoplastic agents, such as fluorouracil (5-FU) and gemcitabine; (23) hormonal antineoplastics, such as goserelin, leuprolide, and tamoxifen; (24) natural antineoplastics, such as aldesleukin, interleukin-2, docetaxel, etoposide, interferon; paclitaxel, other taxane derivatives, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) α-blocker sympatholytics, such as prazosin; (34) D-blocker sympatholytics, such as atenolol; (35) adrenergic sympathomimetics, such as albuterol and dobutamine; (36) cardiovascular agents, such as aspirin (ASA) (enteric coated ASA); (37) D-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as (41) class I antiarrhythmics, such as lidocaine, mexiletine, phenytoin, procainamide, and quinidine; (42) class antiarrhythmics II, such as atenolol, metoprolol, propranolol, and timolol; (43) class III antiarrhythmics, such as amiodarone; (44) class IV antiarrhythmics, such as diltiazem and verapamil; (45) antihypertensives, such as prazosin; (46) angiotensin-converting enzyme inhibitor (ACE inhibitor) antihypertensives, such as captopril and enalapril; (47) antihypertensives, such as atenolol, metoprolol, nadolol, and propanolol; (48) calcium-channel blocker antihypertensive agents, such as diltiazem and nifedipine; (49) central-acting adrenergic antihypertensives, such as clonidine and methyldopa; (50) diuretic antihypertensive agents, such as amiloride, furosemide, hydrochlorothiazide (HCTZ), and spironolactone; (51) peripheral vasodilator antihypertensives, such as minoxidil; (52) antilipemics, such as gemfibrozil and probucol; (53) bile acid sequestrant antilipemics, such as cholestyramine; (54) reductase inhibitor antilipemics, such as lovastatin and pravastatin; (55) inotropes, such as amrinone, dobutamine, and dopamine; (56) cardiac glycoside inotropes, such as (57) thrombolytic agents, such as alteplase, anistreplase, streptokinase, and urokinase; (58) dermatological agents, such as colchicine, isotretinoin, methotrexate, minoxidil, tretinoin (59) dermatological corticosteroid anti-inflammatory agents, such as betamethasone and dexamethasone; (60) antifungal topical anti-infectives, such as amphotericin clotrimazole, miconazole, and nystatin; (61) antiviral topical anti-infectives, such as acyclovir; (62) topical antineoplastics, such as (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes and (69) thrombolytic enzymes, such as alteplase, anistreplase, streptokinase and urokinase; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) H2-blocker anti-ulcer agents, such as cimetidine, famotidine, nizatidine, ranitidine; (74) digestants, such as pancrelipase; (75) prokinetic agents, such as erythromycin; (76) opiate agonist intravenous anesthetics such as fentanyl; (77) hematopoietic antianemia agents, such as (G-CSF), and (GM-CSF); (78) coagulation agents, such as factors 1-10 (A1IF 1-10); (79) anticoagulants, such as warfarin; (80) thrombolytic enzyme coagulation agents, such as alteplase, anistreplase, streptokinase and urokinase; (81) hormones and hormone modifiers, such as bromocriptine; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadotropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin 1M, IMIG, IGIM and immune globulin IVIG; (94) amide local anesthetics, as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs such as diclofenac, ibuprofen, ketoprofen, ketorlac, and naproxen; (99) skeletal muscle relaxants, such as and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenytoin, and valproic acid; (103) barbiturate anticonvulsants, such as phenobarbital and primidone; (104) benzodiazepine anticonvulsants, such as clonazepam, diazepam, and lorazepam; (105) anti-agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) anti-glaucoma agents, such as timolol; (110) mitotic anti-glaucoma agents, such as pilocarpine; (111) ophthalmic aminoglycoside anti-infectives, such as gentamicin, neomycin, and tobramycin; (112) ophthalmic quinolone anti-infectives, such as ciprofloxacin, norfloxacin, and ofloxacin; (113) ophthalmic corticosteroid anti-agents, such as dexamethasone and prednisolone; (114) ophthalmic nonsteroidal anti-inflammatory drugs such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) such as codeine; (119) bronchodilators, such as (120) adrenergic agonist bronchodilators, such as albuterol; (121) respiratory corticosteroid anti-inflammatory agents, such as dexamethasone; (122) antidotes, such as flumazenil and naloxone; (123) heavy metal agents, such as penicillamine; (124) deterrent substance abuse agents, such as disulfiram, naltrexone, and nicotine; (125) withdrawal substance abuse agents, such as bromocriptine; (126) minerals, such as iron, calcium, and magnesium; (127) vitamin B compounds, such as cyanocobalamin (vitamin B12) and niacin (vitamin B3); (128) vitamin C compounds, such as ascorbic acid; and (129) vitamin D such as calcitriol.

Further, recombinant or cell-derived proteins may be used, such as recombinant beta-glucan; bovine immunoglobulin concentrate; bovine superoxide dismutase; formulation comprising fluorouracil, epinephrine, and bovine collagen; recombinant hirudin (r-Hir), HIV-1 immunogen; recombinant human growth hormone recombinant EPO (r-EPO); gene-activated EPO (GA-EPO); recombinant human hemoglobin (r-Hb); recombinant human mecasermin (r-1GF-1); recombinant interferon α; lenograstim (G-CSF); olanzapine; recombinant thyroid stimulating hormone (r-TSH); and topotecan.

Still further, the following listing of peptides, proteins, and other large molecules may also be used, such as interleukins 1 through 18, including mutants and analogues; interferons a, y, and those which may be useful for cartilage regeneration, hormone releasing hormone (LHRH) and analogues, gonadotropin releasing hormone transforming growth factor (TGF); fibroblast growth factor (FGF); tumor necrosis factor-α; nerve growth factor (NGF); growth hormone releasing factor (GHRF), epidermal growth factor (EGF), connective tissue activated osteogenic factors, fibroblast growth factor homologous factor (FGFHF); hepatocyte growth factor (HGF); insulin growth factor (IGF); invasion inhibiting factor-2 (IIF-2); bone morphogenetic proteins 1-7 (BMP 1-7); somatostatin; thymosin-a-y-globulin; superoxide dismutase (SOD); and complement factors, and biologically active analogs, fragments, and derivatives of such factors, for example, growth factors.

Members of the transforming growth factor (TGF) supergene family, which are multifunctional regulatory proteins, may be incorporated in a polymer matrix of the present invention. Members of the TGF supergene family include the beta transforming growth factors (for example, TGF-131, TGF-132, TGF-133); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (1GF)), (for example, lnhibin A, lnhibin B), growth differentiating factors (for example, GDF-1); and Activins (for example, Activin A, Activin B, Activin AB). Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Various forms of the biologically active agents may be used. These include, without limitation, such forms as uncharged molecules, molecular complexes, salts, ethers, esters, amides, prodrug forms and the like, which are biologically activated when implanted, injected or otherwise placed into a subject.

The term "aliphatic" is an art-recognized term and includes linear, branched, and cyclic alkanes, alkenes or alkynes. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer carbon atoms. Likewise cycloalkyls have from about 3 to about 10 carbon atoms in their ring structure, and alternatively about 5, 6 or 7 carbons in the ring structure.

Moreover, the term "alkyl" (or "lower alkyl") includes both "unsubstituted alkyls" and "substituted alkyls," the latter of which refers to alkyl moieties having substituents replacing hydrogen on one or more carbons of the hydrocarbon backbone. Such substituents may include, for example, a halogen, a hydroxyl, a carbonyl (such as a carboxyl, an alkoxycarbonyl, a formyl or an acyl), a thiocarbonyl (such as a thioester, a thioacetate, or a thioformate), an alkoxyl, a phosphoryl, a phosphonate, a phosphinate, an amino, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls may be further substituted with alkyls, alkenyls, alkoxys, alkylthios, aminoalkyls, carbonyl-substituted alkyls, —$CF_3$, —CN and the like.

The term "aralkyl" is art-recognized, and includes aryl groups (e.g., an aromatic or heteroaromatic group).

The terms "alkenyl" and "alkynyl" are art-recognized, and in an organic molecule, generally includes an atom of any element other than carbon or hydrogen. Illustrative heteroatoms include boron, nitrogen, oxygen, phosphorus, sulfur, and selenium.

The term "aryl" is art-recognized, and includes 5-, 6-, and 7-membered single ring aromatic groups that may include from zero to four heteroatoms, for example, benzene, pyrole, furan, thiophene, imidazole, oxazole, thiazole, triazole, pyrazole, pyridine, pyrazine, pyridazine and pyrimidine, and the like. Thos aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydyl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $-CF_3$, $-CN$ or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls, and/or heterocyclyls, or rings joined by non-cyclic moieties.

The terms "ortho," "meta" and "para" are art-recognized and apply to 1,2-, 1,3- and 1,4-disubstituted cyclohexanes, respectively. For example, the names 1,2-dimehtylbenzene and ortho-dimethylbenzene are synonymous.

The terms "heterocyclyl" and "heterocyclic group" are art-recognized, and include 3- to about 10-membered ring structures, such as 3- to about 7-membered rings, whose ring structures include one to four heteroatoms. Heterocycles may also be polycycles. Heterocycclyl groups include, for example, thiophene, thianthrene, furan, pyran, isobenzofuran, chromene, xanthene, phenoxanthin, pyrrole imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphtyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones and the like. The heterocyclic ring may be substituted at one or more positions with such substituents as described above, as for example, halogen, alkyl aralkyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $-CD_3$, $-CN$ or the like.

The terms "polycyclyl" and "polycyclic group" are art-recognized and include structures with two or more rings (e.g., cycloalkyls, cycloalkenyls, cycloalkynyls, aryls and/or heterocyclyls) in which two or more carbons are common to two adjoining rings, e.g., the rings are "fused rings." Rings that are joined through non-adjacent atoms, e.g., three or more atoms are common to both rings, are termed "bridged" rings. Each of the rings of the polycycle may be substituted with such substituents as described above, as for example, halogen, alkyl, aralkyl, alkenyl, alkynyl, cycloalkyl, hyroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $-CD_3$, $-CN$ or the like.

The term "carbocycle" is art-recognized and includes an aromatic or non-aromatic ring in which each atom of the ring is carbon. The following art-recognized terms have the following meanings: "nitro" means $-NO_2$; the term "halogen" designates $-F$, $-Cl$, $-Br$, or $-I$; the term "sulfhydryl" means $-SH$; the term "hydroxyl" or "hydroxy" means $-OH$; and the term sulfonyl" means $-SO_2-$.

The terms "amine" and "amino" are art-recognized and include both unsubstituted and substituted amines. A primary amine carries two hydrogens, a secondary amine, one hydrogen and another substituent and a tertiary amine, the two hydrogens are substituted. The substituents for one or both of the hydrogens can be, for example, and alkyl, an alkenyl, and aryl, a cycloalkyl, a cycloalkenyl, a heterocycle, a polycycle and so on. If both hydrogens are substituted with carbonyls, the carbonyl framed nitrogen forms an imide.

The term "alkylamine" includes an amine group, as defined above, having a substituted or unsubstituted alkyl attached thereto.

The term "amido" is art-recognized as an amino-substituted carbonyl.

The term "alkylthio" is art-recognized and includes and alkyl group, as defined above, having a sulfur radical attached thereto. In certain embodiments, the "alkylthio" moiety is represented by one of $-S$-alkyl, $-S$-alkenyl, $-S$-alkynyl and so on. Representative alkylthio groups include methylthio, ethylthio and the like.

The term "carbonyl" is art-recognized and includes a $C=O$ structure. Carbonyls are involved in esters; carboxyl groups; formates; thiocarbonyls; thioesters; thiocarboxylic acids; thioformates; ketones; and aldehydes.

The terms "alkoxyl" and "alkoxy" are art-recognized and include an alkyl group, as defined above, having an oxygen radical attached thereto. Representative alkoxyl groups include methoxy, ethoxy, propyloxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of $-O$-alkyl, $-O$-alkenyl, $-O$-alkynyl and so on.

The term "sulfonate" is art-recognized and includes a moiety wherein a sulfur atom carries two double bonded oxygens and a single bonded oxygen.

The term "sulfate" is art-recognized and includes a moiety that resembles a sulfonate but includes two single bonded oxygens.

The terms "sulfonamide," "sulfamoyl," "sulfonyl," and "sulfoxido" are art-recognized and each can include a variety of R group substituents as described herein.

The terms phosphoramidite" and "phophonamidite" are art-recognized.

The term "selenoalkyl" is art-recognized and includes an alkyl group having a substituted seleno group attached thereto. Exemplary "selenoethers" which may be substituted on the alkyl are selected from one of $-Se$-alkyl, $-Se$-alkenyl, $-Se$-alkynyl and so on.

Substitutions may be made to alkenyl and alkynyl groups to produce, for example, aminoalkenyls, aminoalkynyls, amidoalkenyls, iminoalkenyls, iminoalkynyls, thioalkenyls, thioalkynyls, carbonyl-substituted alkenyls or alkynyls.

A hydrocarbon is an art-recognized term and includes all permissible compounds having at least one hydrogen and one carbon atom. For example, permissible hydrocarbons include acyclic and cyclic, branched and unbranched, carbocyclic and heterocyclic, aromatic and nonaromatic organic compounds that may be substituted or unsubstituted.

The phrase "protecting group" is art-recognized and includes temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed, Greene et al., Protective Groups in Organic Synthesis 2nd ed., Wiley, N.Y., (1991), for example.

The definition of each expression, e.g., alkyl, aryl etc., when it occurs more than once in any structure, is intended to be independent of its definition elsewhere in the same structure unless otherwise indicated expressly or by the context.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms are art-recognized and represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

Accordingly, included within the compounds of the present invention are the tautomeric forms of the disclosed compounds, isomeric forms including enantiomers, stereoisomers, and diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

As defined herein, in one or more embodiments, "contacting" means that the one or more compounds of the present invention are introduced into a sample having at least one cancer cell, and appropriate enzymes or reagents, in a test tube, flask, tissue culture, chip, array, plate, microplate, capillary, or the like, and incubated at a temperature and time sufficient to permit entry of the at least one compound to the cytosol of the cancer cell. Methods for contacting the samples with the compounds, and other specific binding components are known to those skilled in the art, and may be selected depending on the type of assay protocol to be run. Incubation methods are also standard and are known to those skilled in the art.

In another embodiment, the term "contacting" means that at least one or more compounds of the present invention is introduced into a subject, preferably a subject receiving treatment for medical conditions including but not limited to cancers, developmental disorders, inflammatory disorders, autoimmune diseases, or neuro-degenerative disorders, and that at least one compounds is allowed to come in contact with the cancer cells in vivo.

Embodiments of the invention also include a process for preparing pharmaceutical products comprising the compounds. The term "pharmaceutical product" means a composition suitable for pharmaceutical use (pharmaceutical composition), as defined herein. Pharmaceutical compositions formulated for particular applications comprising the compounds of the present invention are also part of this invention, and are to be considered an embodiment thereof.

In accordance with an embodiment, the present invention provides the use of the any of the compounds of formula I, II and III or T388, or the pharmaceutical composition comprising the same for inhibition of PBX1-DNA interaction in a mammalian cell or population of cells, comprising contacting the cell or population of cells with an effective amount of the compounds of formula I, II and III or T388, or the pharmaceutical composition comprising the same.

In accordance with an embodiment, the present invention provides the use of the any of the compounds of formula I, II and III or T388, or the pharmaceutical composition comprising the same for treating medical conditions including but not limited to cancers, developmental disorders, inflammatory disorders, autoimmune diseases, or neuro-degenerative disorders in a subject comprising administering to the subject an effective amount of the compounds of formula I, II and III or T388, or the pharmaceutical composition comprising the same.

In accordance with an embodiment, the present invention provides the use of the any of the compounds of formula I, II and III or T388, or the pharmaceutical composition comprising the same for treating medical conditions including but not limited to cancers, developmental disorders, inflammatory disorders, autoimmune diseases, or neuro-degenerative disorders in a subject comprising administering to the an effective amount of the compounds of formula I, II and III or T388, or the pharmaceutical composition comprising the same, and an effective amount of at least one other biologically active agent.

As used herein, the term "treat," as well as words stemming therefrom, includes preventative as well as disorder remitative treatment. The terms "reduce," "suppress," "prevent," and "inhibit," as well as words stemming therefrom, have their commonly understood meaning of lessening or decreasing. These words do not necessarily imply 100% or complete treatment, reduction, suppression, or inhibition.

With respect to pharmaceutical compositions described herein, the pharmaceutically acceptable carrier can be any of those conventionally used, and is limited only by physicochemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, injectable organic cosolvents, surfactants, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, saline solution, Ringer's dextrose, dextrose and sodium chloride, lactated Ringer's and fixed oils. Formulations suitable for parenteral administration include, for example, aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), antioxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of the compounds, salts, solvates, or stereoisomers of any one the compounds of Formula I, II, III, and T388 as set forth above, administered should be sufficient to effect, e.g., a therapeutic or prophylactic response, in the subject over a reasonable time frame. The dose will be determined by the efficacy of the particular compound and the condition of a human, as well as the body weight of a human to be treated.

The dose of the compounds, salts, solvates, or stereoisomers of any one the compounds of Formula I, II, III, and T388 as set forth above, of the present invention also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compound can be about 0.001 to about 1000 mg/kg body weight of the subject being treated/day.

In an embodiment, the term "administering" means that the compounds of the present invention are introduced into a subject, preferably a subject receiving treatment for a disease, and the compounds are allowed to come in contact with the one or more disease related cells or population of cells in vivo. In some embodiments the host cell or population of cells in the host can be any cell or population of cells that can be selectively bound by the antigens bound to the compounds of formula I, II, III, and T388 described above. One of ordinary skill in the art would understand the host cells can be cancer cells.

EXAMPLES

The following examples are provided to illustrate embodiments of the present invention but are by no means intended to limit its scope.

FIG. 1. Synthesis of TCRS-362, TCRS-363, and TCRS-364.

As shown in FIG. 1, the synthesis was performed starting with commercially available 1. The key to this reaction was the initial in situ free base of 1 (0-22° C.) followed by the drop-wise addition of acid chloride 2 at 0° C. to form amide 3 exclusively and minimize the undesired bis-acylated product. Subsequent ether formation followed by ester saponification afforded free acid 5, which can be directly isolated as a precipitate from the reaction mixture at pH~5. PyBop coupling with the respective aniline in DMF afforded aryl ethers 7, 9, and 11, as a precipitate from ice/water. The final methyl ether deprotection, under continuous 0° C. to avoid reaction at the undesired methylene ether, afforded the final desired targets TCRS-362, TCRS-363 and TCRS-364, which were purified by reverse phase chromatography due to poor solubility in organic solvents.

Figure 2:
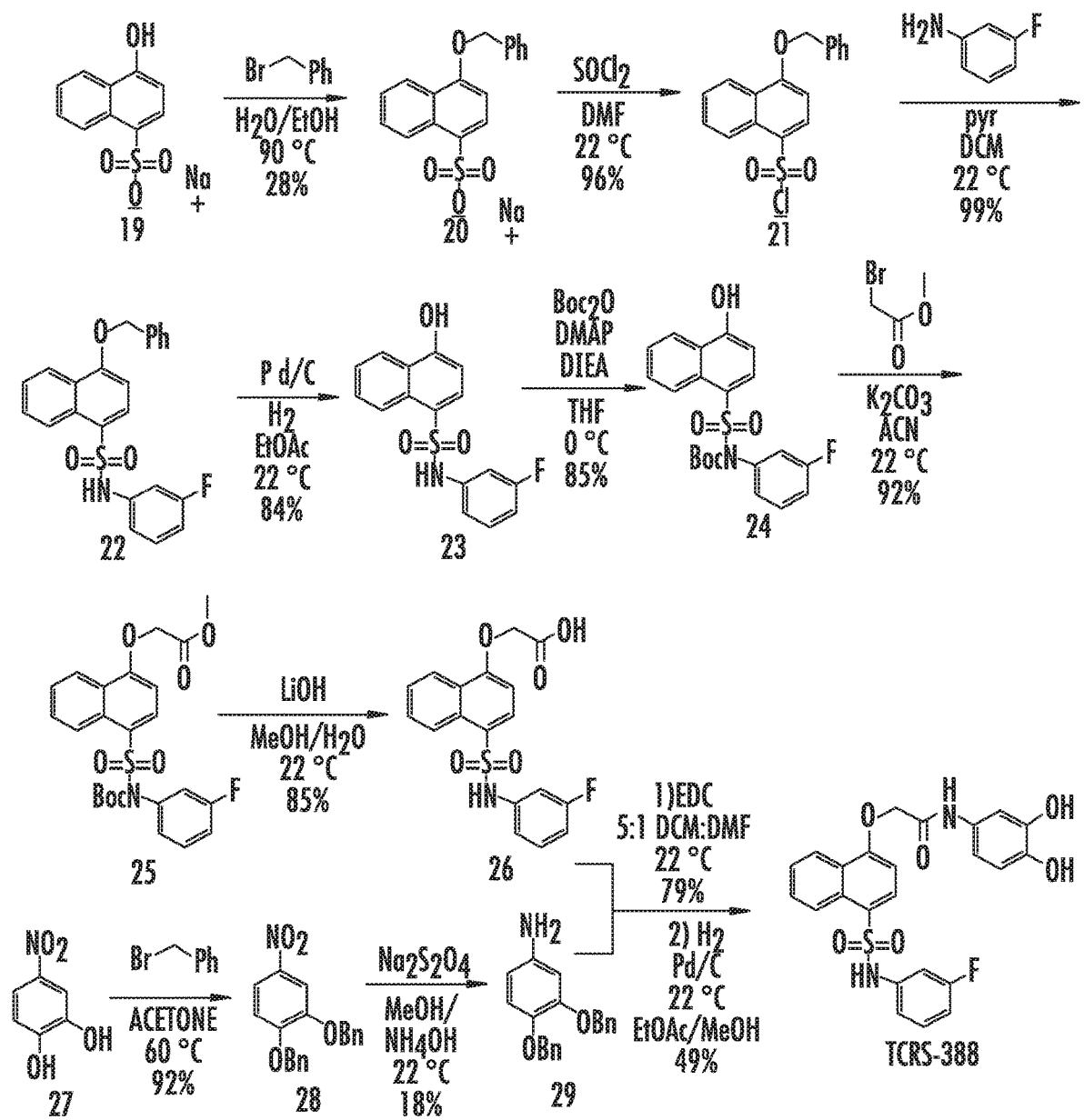
FIG. 2 is a schematic depicting the general synthesis of synthesis of TCRS-388.

FIG. 2. Synthesis of TCRS-388.

As shown in FIG. 2, starting material 19 was converted to the sulfonamide 23 in four steps based on the procedures in WO2013/113489. It was then necessary to protect the sulfonamide before the alkylation of the phenol to prevent indiscriminant alkylation. Saponification of ester 25, accompanied by in situ Boc deprotection, afforded acid 26 directly. The desired product could not be obtained from methyl ether deprotection as the molecule was not stable to the boron tribromide reaction conditions. Therefore, the benzyl protected aniline was prepared from commercially available nitro catechol 27 through benzylation followed by reduction of the nitro group to afford aniline 29. EDC coupling provided the desired bis-benzyl compound which was then deprotected using hydrogenolysis conditions to afford TCRS-388.

Figure 3:
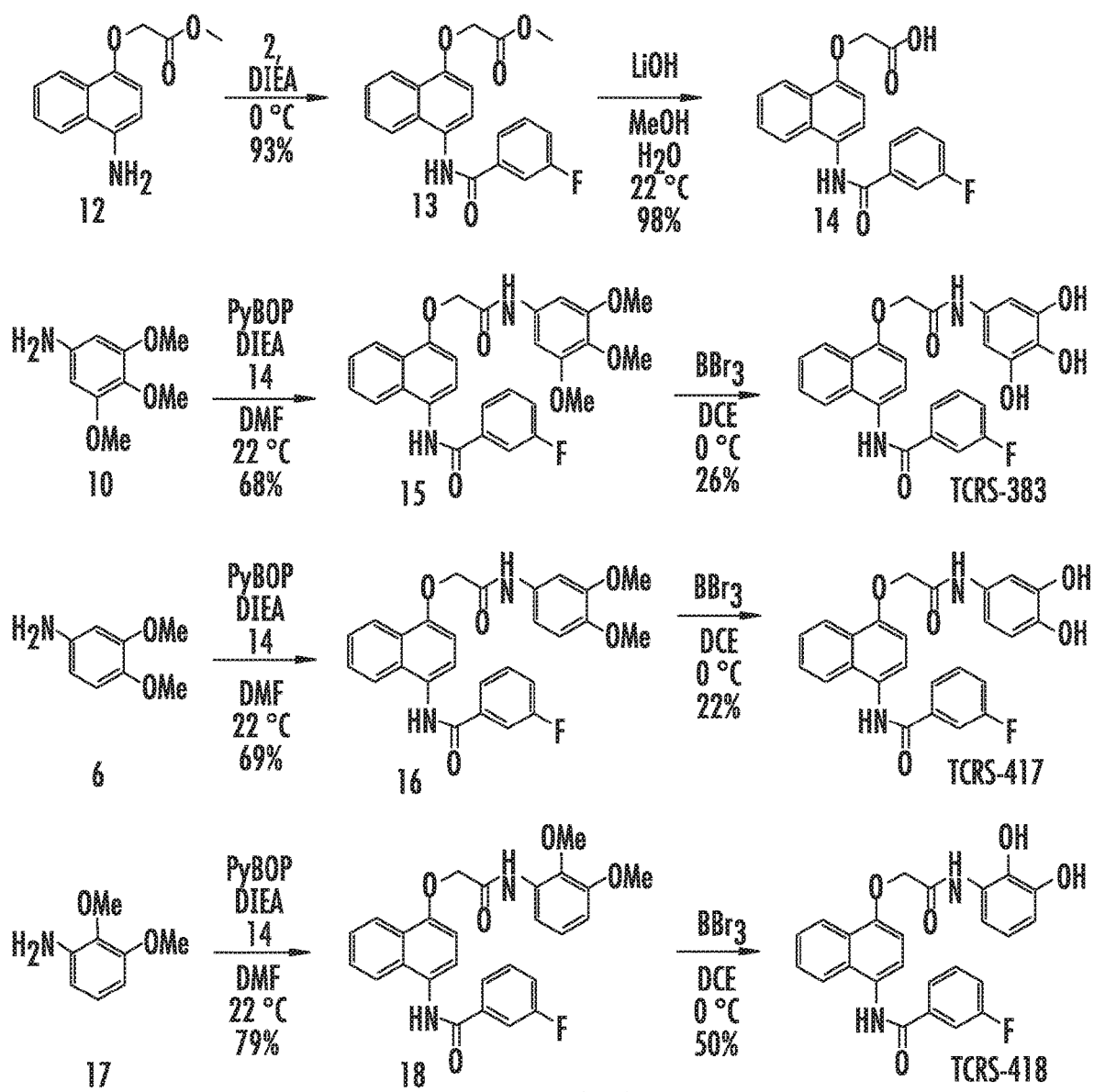
FIG. 3 is a schematic depicting the general synthesis of synthesis of TCRS-383, TCRS-417, and TCRS-418.
Figure 4A:
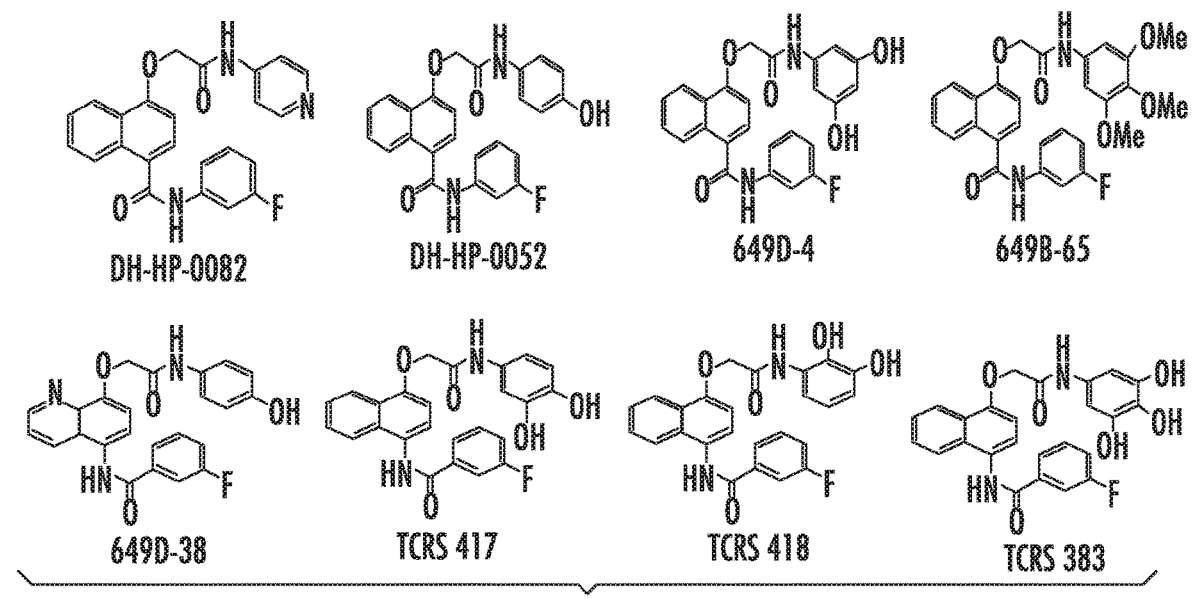
FIGS. 4A-4B illustrates PBX inhibitor analogs (A) and their efficacy in disrupting PBX1-DNA binding complex as determined by the EMSA assay (B). PBX1 nuclear extract was incubated with biotin-labeled PBX1 DNA binding probe in the presence of various concentrations of the compounds. The results indicate that DH52, D4, T383, T417, and T418 are useful as effective drugs.
Figure 4B:
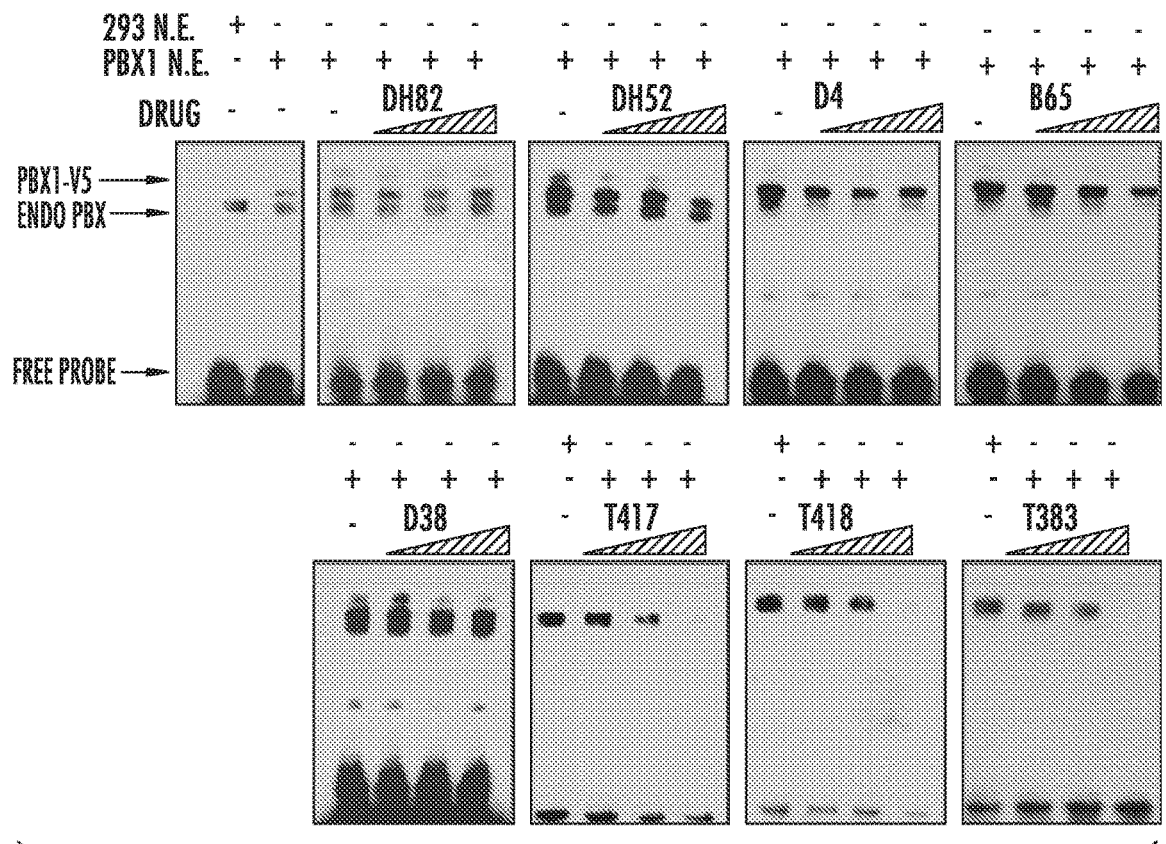
Figure 5:
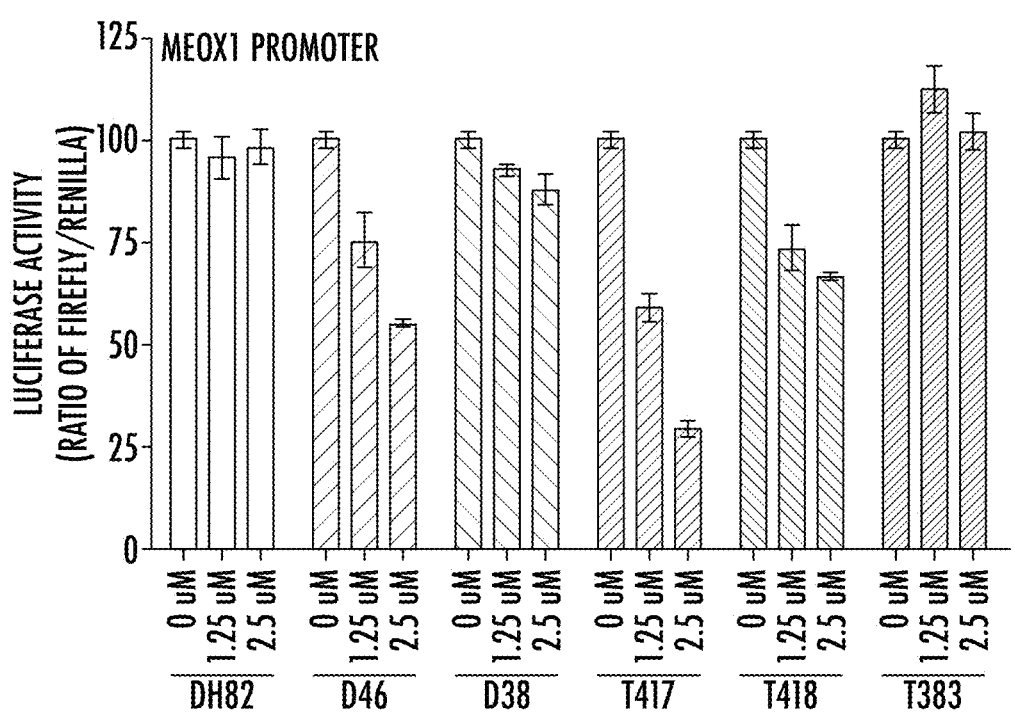
FIG. 5 shows the ability of PBX inhibitors of the present invention to suppress PBX1 transcriptional activities. Promoter of a PBX1 direct target gene, MEOX1, was cloned into a luciferase plasmid, pGL3, and was transfected into 293 cells together with pRenilla, a control plasmid. Twenty-four hours after, luciferase activity was measured using the Dual-Luciferase reporter assay system.
Figure 6:
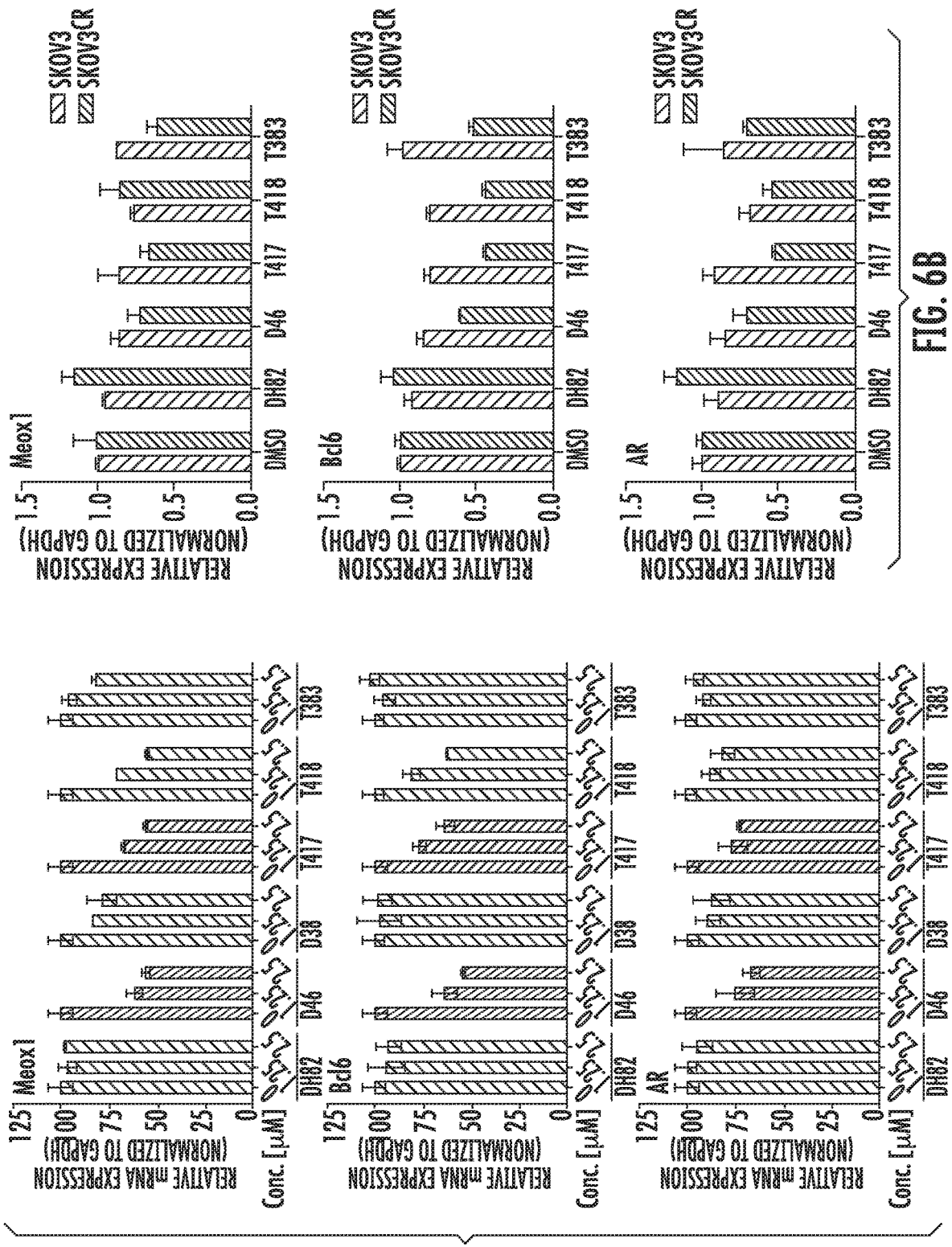
FIG. 6A-6B depicts the ability of PBX inhibitors to suppress expression of PBX1 direct target genes, MEOX1, BCL6, and AR. OVCAR3 cells (A) were incubated with PBX inhibitors at 0, 1.25, and 2.5 µM concentrations for 24 hr. PBX1-overexpressing SKOV3 carboplatin-resistant and parental cells (B) were incubated with 2.5 µM of PBX1 inhibitors for 24 hr. RT-PCR was performed using gene-specific primers. Data were normalized to data obtained using a house keeping gene, GAPDH.
Figure 7:
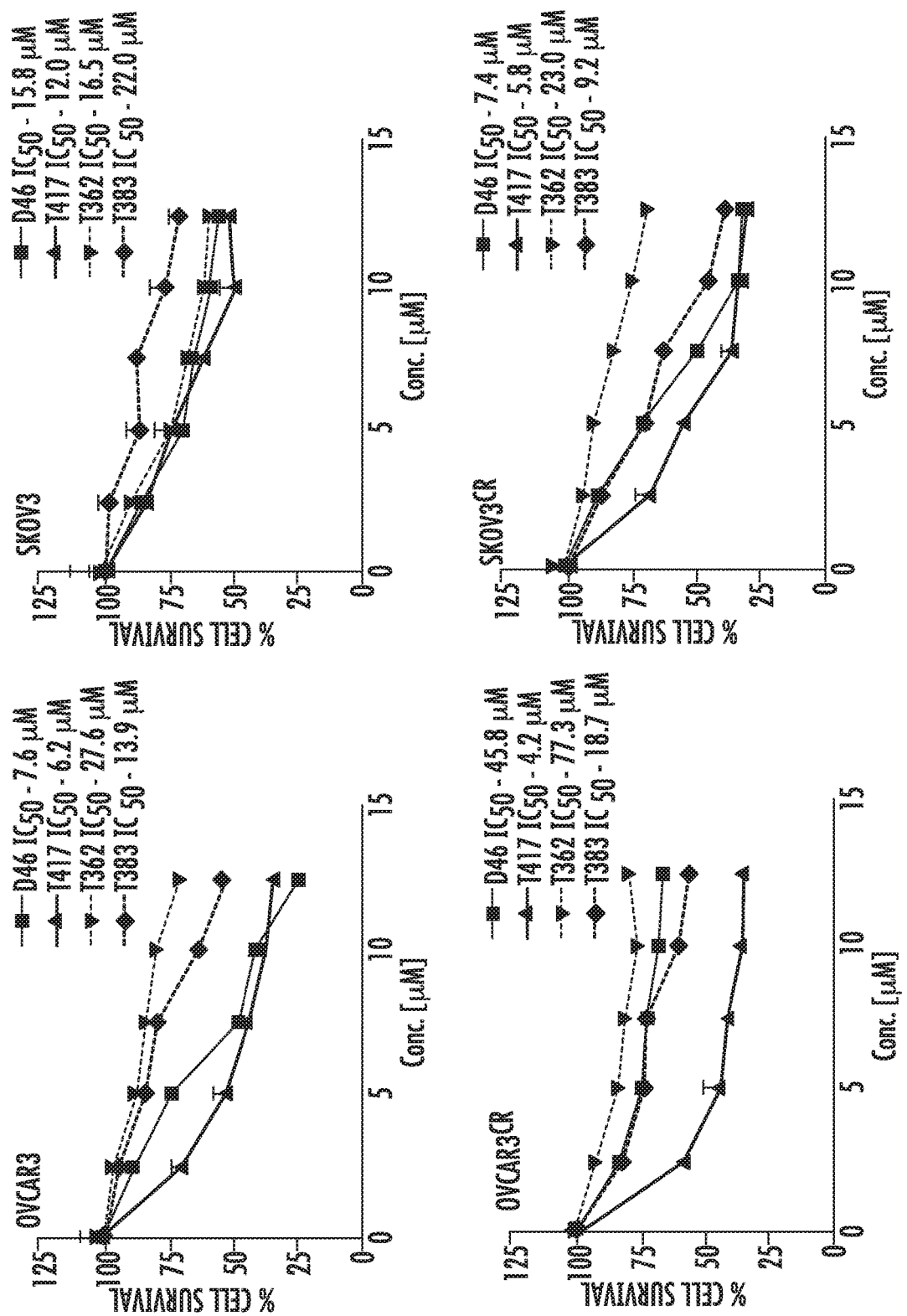
FIG. 7 depicts a cytotoxicity assay in ovarian cancer cells using PBX inhibitors. Ovarian cancer cells were incubated with serial concentrations of PBX inhibitors for 48 hr. Relative live cell numbers were determined by a Cell-Titer Blue assay and were normalized to cell numbers measured at 0 µM. Prodrugs including DH82 and D38 were included as controls. CR represents a carboplatin-resistant cell variant established from parental naive cells. PBX1 overexpresses in the CR cells in comparison to parental control cells (Western blot shown in FIG. 10).
Figure 8B:
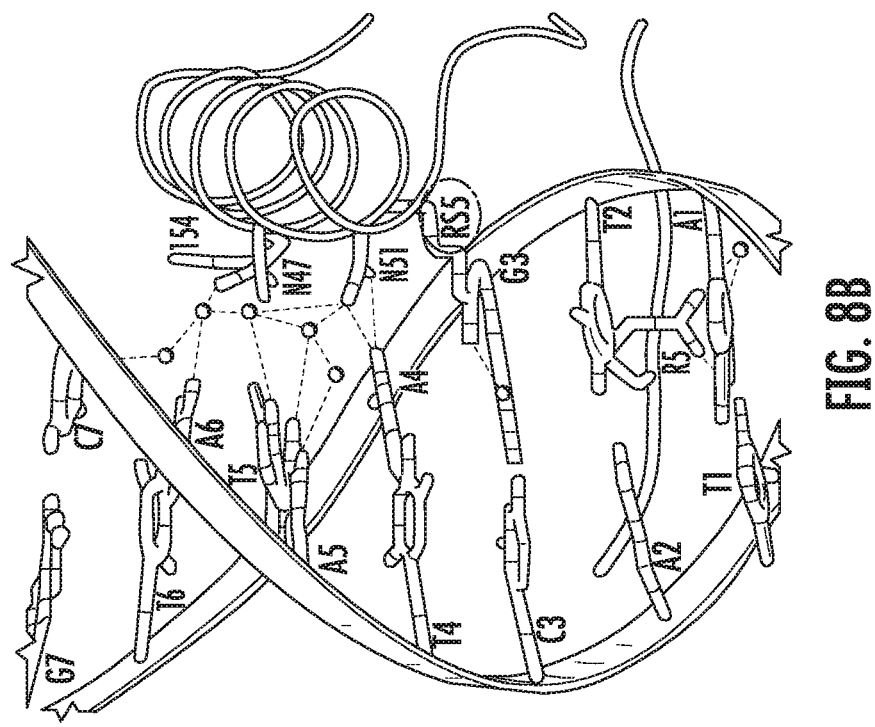
FIG. 8B shows DNA-PBX1 protein contact revealed by crystal study 8. Dotted lines indicate hydrogen bonds. The blue coil represents the 3rd helix of the PBX1 protein. I54 and N47 also form Van der Waals interactions with DNA. N47 is colored in yellow, and N51 is colored in blue.
Figure 8A:
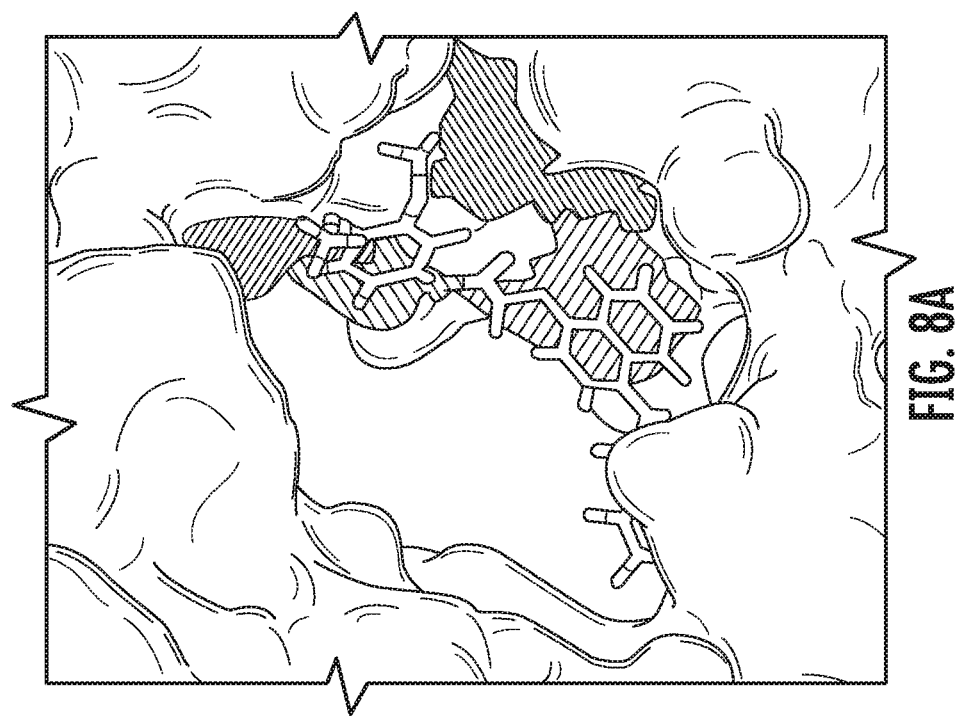
FIG. 8A is an unsupervised docking analysis of a PBX1 inhibitor in the DNA-PBX1 complex. The first benzene ring in the compound contacts R55 (colored in red) on the PBX1 protein, while the naphthalene backbone of the compound interacts with I54 (colored in green), likely through van der Waals forces.
Figure 10:
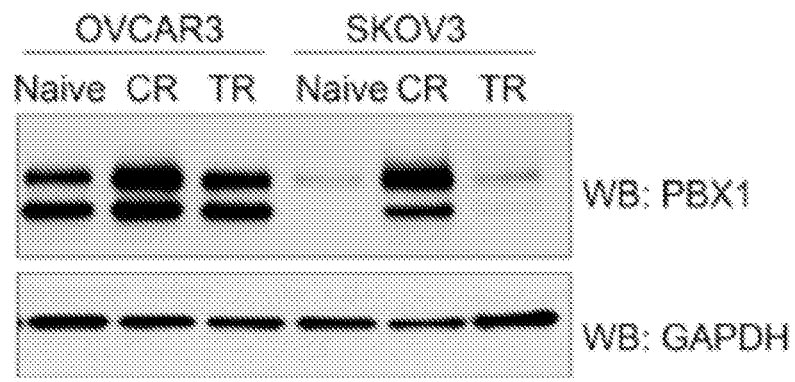
FIG. 10 shows PBX1 expression in chemoresistant ovarian cancer cell lines. Ovarian cancer cell lines, OVCAR3 and SKOV3, were continuously treated with low dose carboplatin and paclitaxel for 2 months, and PBX1 expression was measured by Western blot. CR indicates carboplatin-resistant and TR represents paclitaxel resistant cells. PBX1 overexpresses in the CR cells as compared to parental naive cells or TR cells.
Figure 11A:
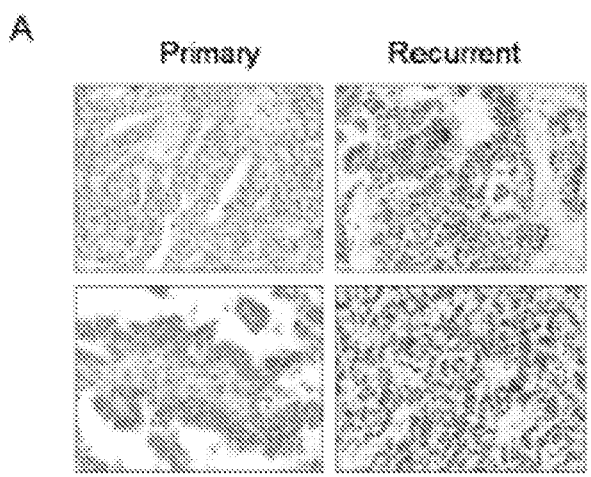
FIG. 11 illustrates that PBX1 is more highly overexpressed in recurrent ovarian cancer patients than in primary ovarian cancer patients. 11A. Two representative paired primary and recurrent ovarian serous carcinoma tissues are shown. Highly nuclear staining was observed in recurrent ovarian carcinoma tissues. 11B. Immunointensity was independently scored by two investigators. Based on H score, PBX1 is more highly expressed in recurrent ovarian serous carcinoma tissues than paired primary ovarian serous carcinoma tissues (Paired t-test p<0.01).
Figure 11B:
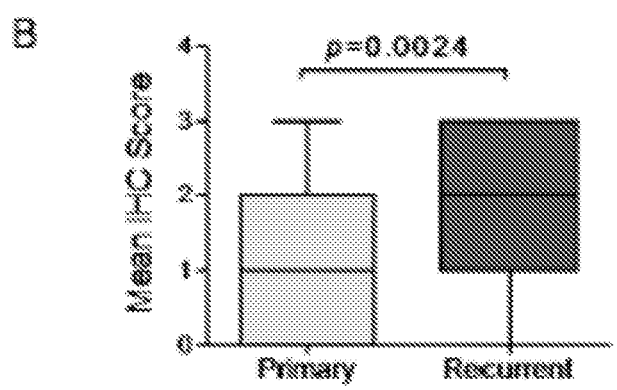
Figure 12:
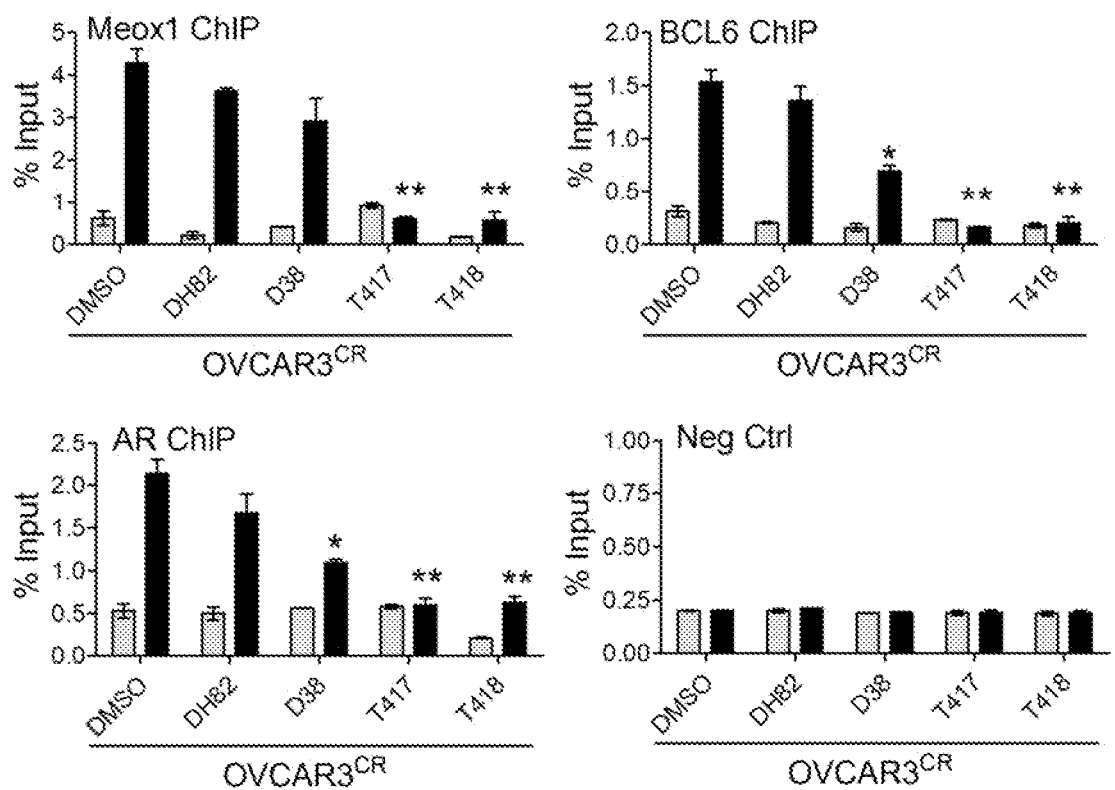
FIG. 12 depict that PBX inhibitors disrupt the binding of PBX1/DNA complex in the promoter region of PBX1 direct target genes, MEOX1, BCL6, and AR, determined by the Chromatin Immunoprecipitation (ChIP) qPCR analysis. Carboplatin-resistant OVCAR3 cells were treated with 2 µM of each PBX1 inhibitors for 24 hr, and occupancy of target gene promoters by PBX1 was assessed by ChIP-qPCR assay to amplify the promoter regions of PBX1 direct target genes. PCR was performed in triplicated wells, normalized to input control, and presented as mean±SD; *p<0.05, **p<0.01, Student's t-test.
Figure 13A:
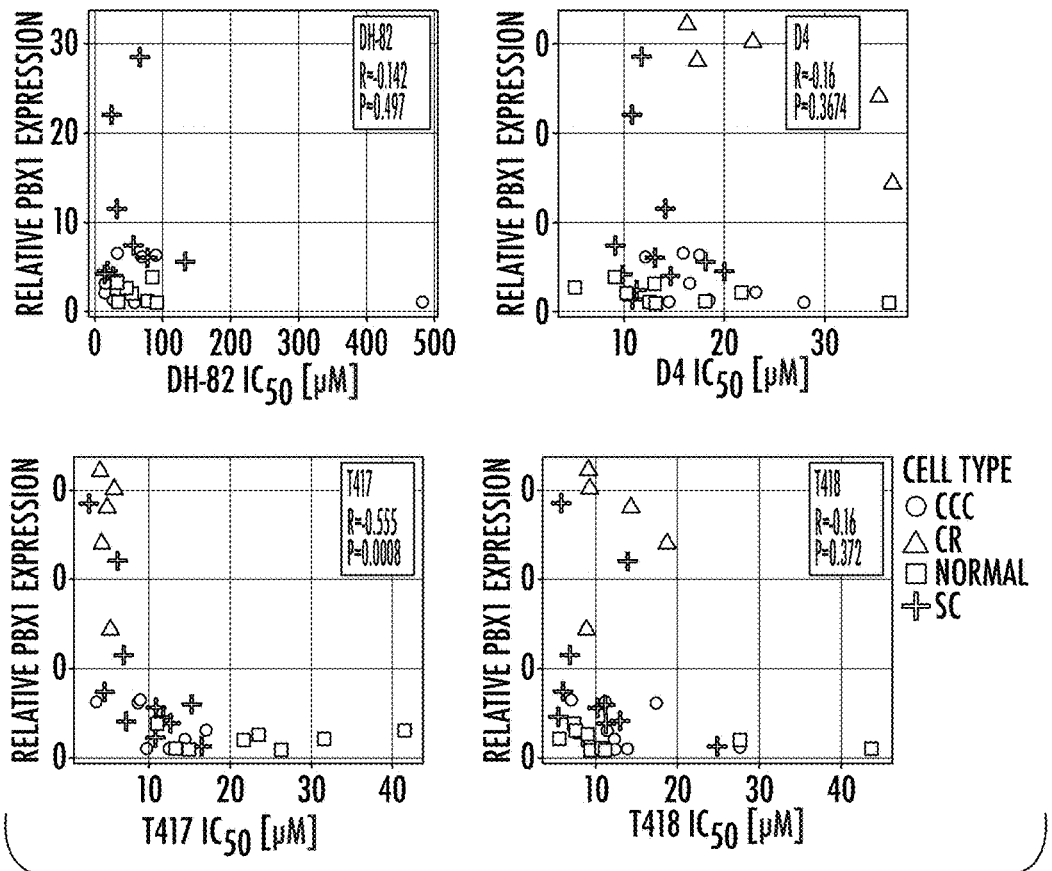
FIGS. 13A-13B show the levels of PBX1 expression in cancer cells correlate with their response to T417, but not to the prodrugs including DH-82, D4, and T418. (A) Cytotoxicity assay in ovarian cancer cell lines incubated with the indicated PBX1 inhibitor. Relative live cell numbers were determined by a Cell-Titer Blue assay and were normalized to cell numbers measured in the vehicle control-treated group. $IC_{50}$ values of individual cell lines were calculated. Each data point represents relative PBX1 expression level and corresponding $IC_{50}$ value for each cell r represents Pearson's correlation coefficient, and p represents two-sided Student's t-test. Primary cultures of ovarian cancer directly derived from patients were established and PBX1 expression was determined by the Western blot analysis (B). Their cytotoxic sensitivity toward T417 was assessed and the $IC_{50}$ value of each primary cell culture calculated. The relationship between PBX1 expression and $IC_{50}$ value for each primary cell culture was plotted and the correlation was determined by Pearson analysis.
Figure 13B:
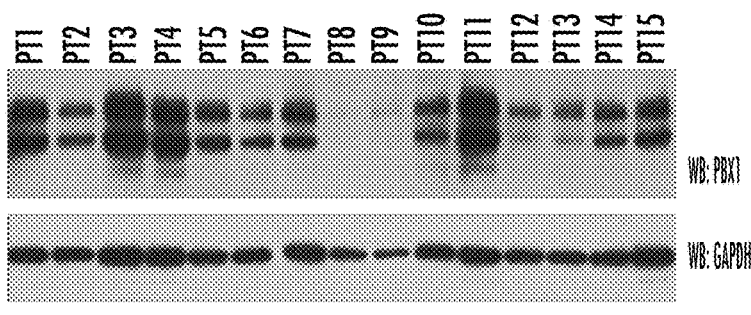
Figure 13C:
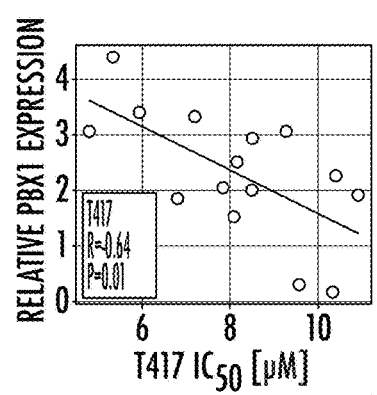
Figure 14A:
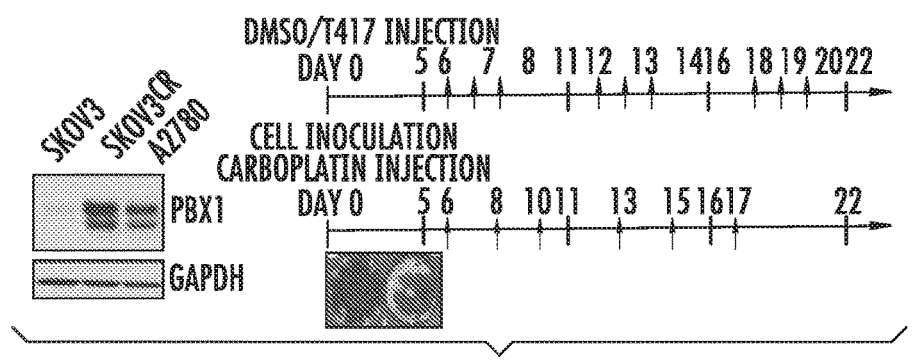
FIGS. 14A-14D depict the anti-tumor effect of T417 on suppressing tumor growth of PBX1-overexpressing A2780 and SKOV3 carboplatin-resistant cancers, but not SKOV3 parental cancer cells. (A) The experimental procedure. A2780Luc and SKOV3CRLuc cells were injected subcutaneously into the athymic nu/nu mice ($3 \times 10^6$, n=8 for each group). Parental SKOV3Luc cells were used as a negative control. Mice were intraperitoneally (i.p.) injected with T417 (red, 2.5 mg/kg/injection) or DMSO (red arrows) using a 3 days-on 4-days off protocol. Carboplatin (30 mg/kg/injection) was administrated i.p. every other day (green arrows). (B) Tumor volume was measured every other day for 25 to 40 days using a caliper, and luminescence activity was evaluated weekly. (C) Endpoint tumor volumes of A2780Luc, SKOV3Luc, and SKOV3CRLuc xenografts treated with the indicated drug or drug combination. Student's t-test. (D) Representative bioluminescence images of tumor burden in SKOV3CRLuc-inoculated mice treated with indicated drug. Images captured by the IVIS Spectrum at day 35. Two mice in each group of SKOV3CRLuc were photographed at day 35 to visually demonstrate tumor growth in each mouse. In vivo bioluminescence images were taken at the same time using the IVIS Spectrum.
Figure 14B:
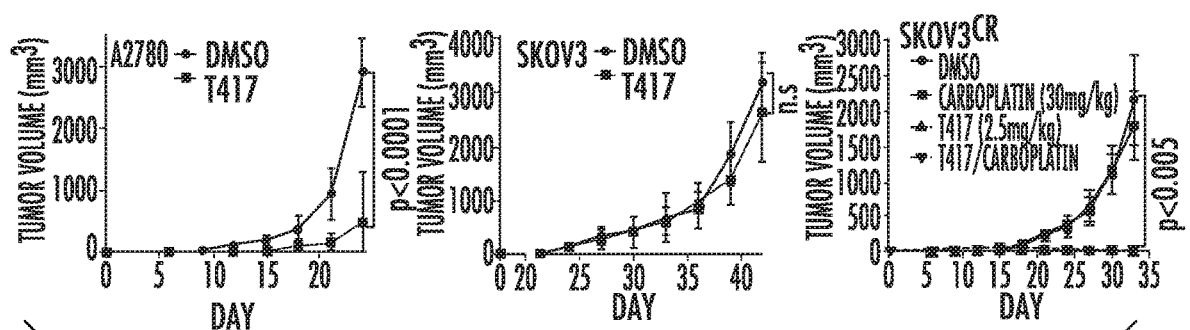
Figure 14C:
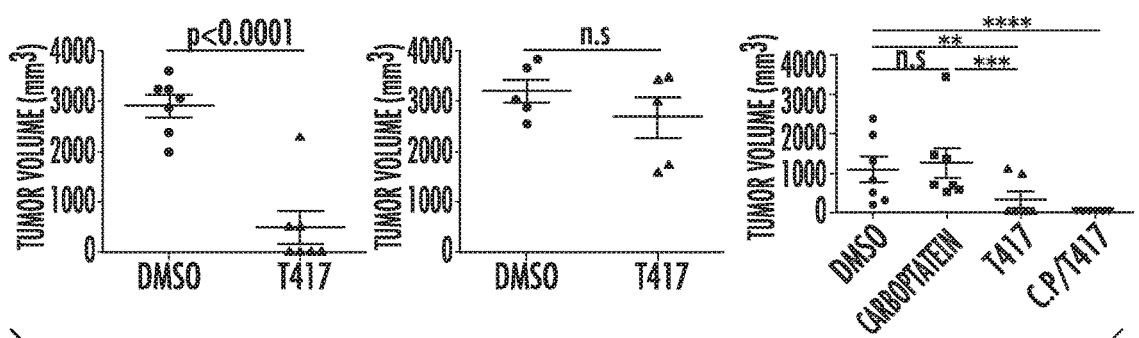
Figure 14D:
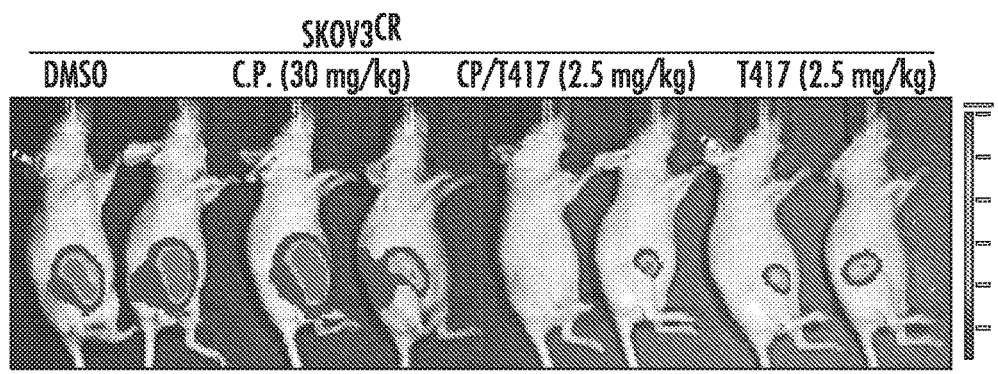

FIG. 3. Synthesis of TCRS-383, TCRS-417, and TCRS-418.

As shown in FIG. 3, commercially available 12 was subjected to similar acylation conditions, as described previously; followed by ester saponification to afford acid 14. Initial 5% citric acid quench provided the desired product a precipitate, which was washed with ether and hexane before further use. PyBop coupling followed by methyl ether deprotection, as described above, afforded TCRS-383, TCRS-417 and TCRS-418. (Note: TCRS-383 was purified by normal phase in 0-10% MeOH in DCM).

Electrophoretic Mobility Shift Assay (EMSA). Nuclear extracts were isolated using the NE-PER nuclear and cytoplasmic extraction reagents (Pierce Biotechnology) after transfection of cells with a PBX1-V5 construct (PloS one. 2012; 7(5): e36054 PMID: 22567123 (2012)), and an EMSA was performed utilizing the LightShift Chemiluminescent EMSA kit (Pierce Biotechnology) following the manufacturer's protocol. For the PBX1-EMSA, biotinylated-DNA probes in the PBX1- or Notch3-binding promoter regions were generated and annealed by Integrated DNA Technology (IDT, Coralville, Iowa). The detailed experiment is described in previous studies (Oncotarget (2010); 1(3): 210-8. PMID: 20953350; Am J Path. (2010), 177(3): 1087-94. PMID: 20671266; Cancer Res. (2012); 72(9): 2294-303. PMID: 22396495). To observe the binding inhibition of the DNA probe/PBX1 protein complex by PBX1-targeting drugs, each sample was incubated with DMSO, 10 μM, 50 μM and 100 μM of each drug before the addition of 20 fmol of biotinylated-DNA probe. For further confirmation of the results from the positive and negative control experiments, purified recombinant PBX1 and CSL proteins were purchased from Origene (Rockville, Md.), and incubated with the same concentrations of each drug.

Luciferase Reporter Assay and Drug Treatment. In the promoter assays, promoter constructs of MEOX1, a downstream genes of PBX1, were generated based on the location of the PBX1-binding motif at −181 bp (TGATGATTAAT) from TSS. 1.37 kb of MEOX1 promoter region was purchased from Genecopia (Rockville, Md.) and further amplified with NheI and XhoI using Pfu Ultra II polymerase (Agilent) to generate the truncated forms of 0.45 kb, 0.7 kb and 1.2 kb in the pGL3-basic vector. All constructs were confirmed by sequencing (Macrogen, Rockville, Md.) and the sequence of cloning primers can be provided upon request.

To measure luciferase activity, 293T and OVCAR3 cells were transfected with pGL3-MX constructs and incubated for 24 hr, and PBX1-targeting drugs at the designated concentration were treated for 24 hr. To compensate for transfection efficiency, pRL-Renilla reporter plasmid (Promega) was cotransfected, and consequently luciferase activity was determined by Dual-Glo luciferase reagent (Promega). The firefly luciferase activity was normalized to the luciferase activity of Renilla.

Chromatin Immunoprecipitation (ChIP) Analysis and qPCR. To confirm the binding inhibition by the drug, chromatin immunoprecipitation (ChIP) assay and quantified PCR were performed to amplify the promoter regions of PBX1 downstream genes after drug treatment. ChIP protocol was modified from previous study. Briefly, $1\times10^7$ OVCAR3 cells were treated with 2 µM of each drug for 24 hr, cross-linked with 1% (vol/vol) formaldehyde for 10 min, lysed in lysis buffer (1% SDS, 10 mM EDTA, 50 mM Tris-HCl, pH 8.0), and sonicated using the Bioruptor (Diagenode, Denville, N.J.). Lysates were incubated with anti-PBX1 antibody overnight with rotation and pulled down using Protein G magnetic beads (Dynabead, Invitrogen), and eluted using the QIAquick PCR Purification Kit (Qiagen). We subjected precipitated DNA to quantitative PCR (Bio-Rad iCyclers, MyIQ, IQ4) with the primers to amplify the promoter regions of PBX1-downstream genes. Fold enrichment was calculated by a $\Delta C(t)$ method and normalized to input according to the formula $(\Delta(C)(t)_{IP} - C(t)_{input})100$.

Western Blot. To measure PBX1 expression levels, we collected cells from normal human and mouse tissues, endometrial epithelial cells (EME), ovarian surface epithelial cells (OSE), fallopian tube epithelial cells (FTE), ovarian clear cell carcinoma (CCC), and low- and high-grade serous carcinoma (LGSC and HGSC). After washing, cells were lysed with lysis buffer (50 mM Tris, ph 8.0, 150 mM NaCl, 1% NP40), supplemented with protease inhibitor cocktail (Thermo Scientific). Cell lysates were separated by SDS-PAGE and transferred onto a PVDF membrane using a semi-dry transfer (Bio-Rad). After blocking with 5% non-fat dry milk in TBST (20 mM Tris-HCl, 0.5 M NaCl, 0.1% Tween 20), samples were incubated overnight with anti-PBX1 antibody subsequently incubated in secondary antibody (Jackson Laboratories, West Grove, Pa.). After developing with ECL solution (Amersham), PVDF membranes were stripped with Restore Western Blot Stripping Solution (Thermo Scientific) and then re-blotted with anti-GAPDH antibody for the control. To calculate PBX1 protein expression levels, the intensity of PBX1 and GAPDH bands were measured using ChemiDoc XRS (Bio-Rad), and calculated through the calculation:

$(Int_{PBX1}/Int_{GAPDH})/lowest(Int_{PBX1}/Int_{GAPDH})$.

Drug Sensitivity and Cell Viability Assay. Cells were seeded in 96-well plate at a density of 3,000 cells/well in triplicate and were treated with 0 µM, 2.5 µM, 5 µM, 7.5 µM and 10 µM of D82, D4, T417 and T418 in 1% FBS-culture medium for 48 hr. Cell viability was measured by either the fluorescence intensity of 0.1% SYBR green I nucleic acid staining solution (Invitrogen) for attaching cells or Cell Titer-Blue reagent (Promega, Madison, Wis.) for cells in suspension, using a microplate reader (Fluostar, BMG, Durham, N.C.). The data were presented as their mean±s.d., calculated from triplicated values, and $IC_{50}$ was defined as the concentration that results in a 50% decrease in the number of cells. Pearson's correlation index was calculated using R (Version 3.0.2) by the intensity ratios of PBX1/GAPDH expression and % inhibition of each drug.

Anti-tumor effect of T417 in vivo. We tested the anti-tumor potency of T417 (FIG. 14) using a platinum-resistant mouse tumor model and found that T417 can also potently suppress tumor growth, while carboplatin is relatively ineffective (FIG. 14). The data support potential clinical application of small molecule compounds developed in this study.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula I:

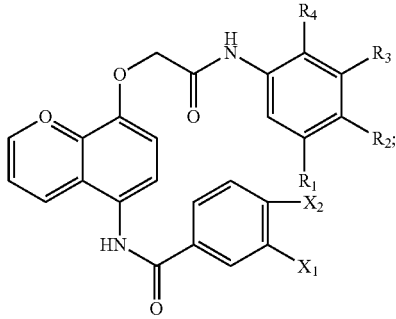

or a salt, solvate or stereoisomer thereof, wherein $R_1$ to $R_4$ are independently H, OH or $OCH_3$, $X_1$ or $X_2$ is either H or a halogen, and Q is either CH or N.

2. A compound of formula II having the following formula:

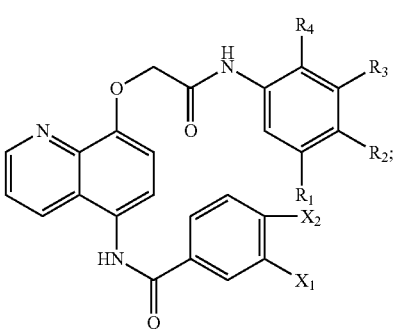

or a salt, solvate or stereoisomer thereof, wherein $R_1$ to $R_4$ are independently H, OH or $OCH_3$, and $X_1$ or $X_2$ is either H or a halogen.

3. A compound selected from the group consisting of:

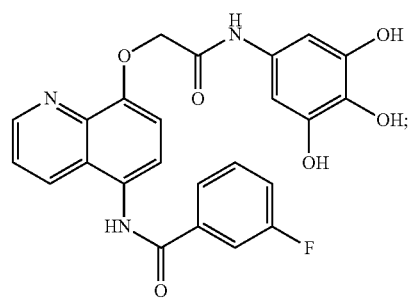

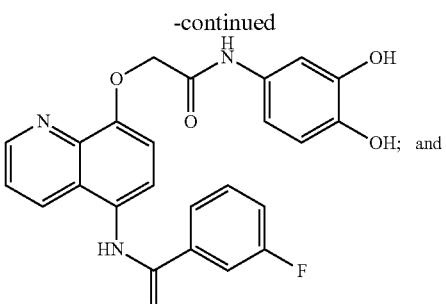

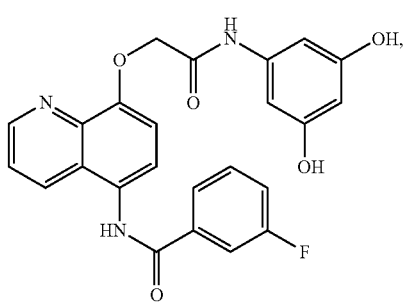

or a salt, solvate or stereoisomer thereof.

4. A compound of formula III having the following formula:

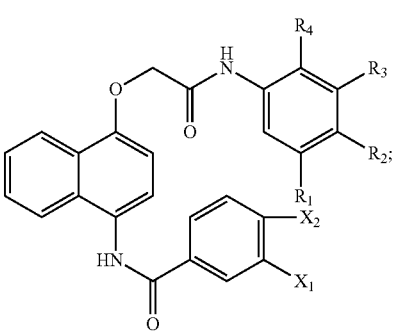

or a salt, solvate or stereoisomer thereof, wherein $R_1$ to $R_4$ are independently H, OH or $OCH_3$, and $X_1$ or $X_2$ is either H or a halogen.

5. A compound selected from the group consisting of:

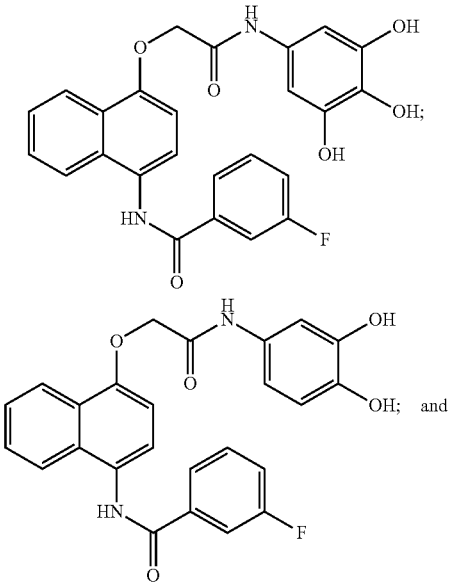

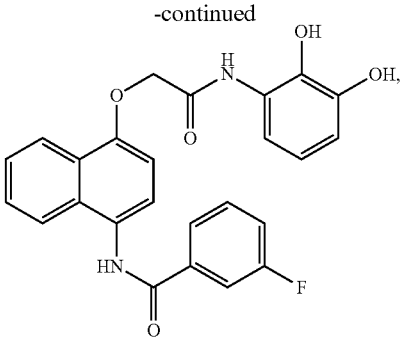

or a salt, solvate or stereoisomer thereof.

6. A pharmaceutical composition comprising the compound of claim 1, and a pharmaceutically acceptable carrier.

7. A pharmaceutical composition comprising the compound of claim 2, and a pharmaceutically acceptable carrier.

8. A pharmaceutical composition comprising the of claim 3, and a pharmaceutically acceptable carrier.

9. A pharmaceutical composition comprising the compound of claim 4, and a pharmaceutically acceptable carrier.

10. A pharmaceutical composition comprising the of claim 5, and a pharmaceutically acceptable carrier.

* * * * *